(12) United States Patent
Chenault

(10) Patent No.: US 8,404,779 B2
(45) Date of Patent: *Mar. 26, 2013

(54) TISSUE ADHESIVE AND SEALANT COMPRISING POLYGLYCEROL ALDEHYDE

(75) Inventor: Henry Keith Chenault, Hockessin, DE (US)

(73) Assignee: Actamax Surgical Materials LLC, Berkeley, CA (US)

( * ) Notice: Subject to any disclaimer, the term of this patent is extended or adjusted under 35 U.S.C. 154(b) by 43 days.

This patent is subject to a terminal disclaimer.

(21) Appl. No.: 13/258,745

(22) PCT Filed: Mar. 26, 2010

(86) PCT No.: PCT/US2010/028833
§ 371 (c)(1),
(2), (4) Date: Sep. 22, 2011

(87) PCT Pub. No.: WO2010/111594
PCT Pub. Date: Sep. 30, 2010

(65) Prior Publication Data
US 2012/0014909 A1    Jan. 19, 2012

Related U.S. Application Data

(60) Provisional application No. 61/164,005, filed on Mar. 27, 2009, provisional application No. 61/164,007, filed on Mar. 27, 2009, provisional application No. 61/164,012, filed on Mar. 27, 2009.

(51) Int. Cl.
*C08G 65/48* (2006.01)
*A61L 24/04* (2006.01)
*A61K 8/90* (2006.01)

(52) U.S. Cl. .................. 525/50; 424/78.37; 424/486

(58) Field of Classification Search .................. None
See application file for complete search history.

(56) References Cited

U.S. PATENT DOCUMENTS

| | | |
|---|---|---|
| 2,026,785 A | 1/1936 | Harris |
| 4,631,055 A | 12/1986 | Redl et al. |
| 5,322,510 A | 6/1994 | Lindner et al. |
| 5,582,596 A | 12/1996 | Fukunaga et al. |
| 5,989,215 A | 11/1999 | Delmotte et al. |
| 6,179,862 B1 | 1/2001 | Sawhney |
| 6,458,147 B1 | 10/2002 | Cruise et al. |
| 6,620,125 B1 | 9/2003 | Redl |
| 6,723,067 B2 | 4/2004 | Nielson |
| 7,347,850 B2 | 3/2008 | Sawhney |
| 2002/0042473 A1 | 4/2002 | Trollsas et al. |
| 2003/0119985 A1 | 6/2003 | Sehl et al. |
| 2005/0002893 A1 | 1/2005 | Goldmann |
| 2006/0078536 A1 | 4/2006 | Kodokian et al. |
| 2007/0031371 A1 | 2/2007 | McManus et al. |
| 2008/0319101 A1 | 12/2008 | Nakajima et al. |

FOREIGN PATENT DOCUMENTS

| | | |
|---|---|---|
| DE | 4117033 | 11/1992 |
| WO | WO 2006/042161 | 4/2006 |
| WO | WO 2008/066787 | 6/2008 |

*Primary Examiner* — Robert A Wax
*Assistant Examiner* — Sarah Park
(74) *Attorney, Agent, or Firm* — McCarter & English

(57) ABSTRACT

A tissue adhesives and sealant formed by reacting a polyglycerol aldehyde with a water-dispersible, multi-arm amine is described. The tissue adhesive and sealant may be useful for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and to prevent post-surgical adhesions.

23 Claims, No Drawings

TISSUE ADHESIVE AND SEALANT COMPRISING POLYGLYCEROL ALDEHYDE

CROSS-REFERENCE TO RELATED APPLICATIONS

This application is a 35 U.S.C. §371 national state filing of International Application No. PCT/US2010/028833, which claims the benefit of and priority under 35 U.S.C. §119 to U.S. Provisional Application Ser. Nos. 61/164,005; 61/164,007 and 61/164,012, all of which were filed Mar. 27, 2009. The entire contents of each of the foregoing applications are incorporated herein by reference.

FIELD OF THE INVENTION

The invention relates to the field of medical adhesives and sealants. More specifically, the invention relates to a tissue adhesive and sealant formed by reacting a polyglycerol aldehyde with a water-dispersible, multi-arm amine.

BACKGROUND OF THE INVENTION

Tissue adhesives and sealants have many potential medical applications, including wound closure, supplementing or replacing sutures or staples in internal surgical procedures, preventing leakage of fluids such as blood, bile, gastrointestinal fluid and cerebrospinal fluid, adhesion of synthetic onlays or inlays to the cornea, drug delivery devices, and as anti-adhesion barriers to prevent post-surgical adhesions. Conventional tissue adhesives and sealants are generally not suitable for a wide range of adhesive applications. For example, cyanoacrylate-based adhesives have been used for topical wound closure, but the release of toxic degradation products limits their use for internal applications. Fibrin-based adhesives are slow curing, have poor mechanical strength, and pose a risk of viral infection. Additionally, fibrin-based adhesives do not bond covalently to the underlying tissue.

Several types of hydrogel tissue adhesives have been developed, which have improved adhesive and cohesive properties and are nontoxic (see for example Sehl et al., U.S. Patent Application Publication No. 2003/0119985, and Goldmann, U.S. Patent Application Publication No. 2005/0002893). These hydrogels are generally formed by reacting a component having nucleophilic groups with a component having electrophilic groups that are capable of reacting with the nucleophilic groups of the first component to form a crosslinked network via covalent bonding. However, these hydrogels typically swell, dissolve away too quickly, or lack sufficient adhesion or mechanical strength, thereby decreasing their effectiveness as surgical adhesives.

Kodokian et al. (copending and commonly owned U.S. Patent Application Publication No. 2006/0078536) describe hydrogel tissue adhesives formed by reacting an oxidized polysaccharide with a water-dispersible, multi-arm polyether amine. These adhesives provide improved adhesion and cohesion properties, crosslink readily at body temperature, maintain dimensional stability initially, do not degrade rapidly, and are nontoxic to cells and non-inflammatory to tissue. However, the instability of oxidized polysaccharides in aqueous solution limits their shelf-life for commercial use. For example, dextran aldehyde undergoes hydrolytic depolymerization much more rapidly than its parent polymer, dextran (E. Schacht et al. *J. Controlled Release*, 1:33-46, 1984; Callant at al. *Reactive Polymers*, 8: 129-136, 1988).

Therefore, the need exists for a tissue adhesive and sealant that has the desirable properties of the hydrogel tissue adhesive described by Kodokian et al., supra, but that is formed using a polymer containing aldehyde groups that is more stable in aqueous solution than oxidized polysaccharides. The need also exists for a tissue adhesive and sealant that comprises a polymer containing aldehyde groups, which is more stable in aqueous solution than oxidized polysaccharides, and that has an adhesive strength that is similar to or greater than those of comparable formulations produced with an oxidized polysaccharide.

SUMMARY OF THE INVENTION

The present invention addresses the above needs by providing a tissue adhesive and sealant that is formed by reacting a polyglycerol aldehyde, which is more stable in aqueous solution than oxidized polysaccharides, with a water-dispersible, multi-arm amine.

Accordingly, in one embodiment, the invention provides a kit comprising:
  a) at least one polyglycerol aldehyde having aldehyde groups, said polyglycerol aldehyde having a number-average molecular weight of about 400 to about 20,000 Daltons and an equivalent weight per aldehyde group of about 100 to about 3,000 Daltons; and
  b) at least one water-dispersible, multi-arm amine wherein at least three of the arms are terminated by at least one primary amine group, wherein the multi-arm amine has a number-average molecular weight of about 450 to about 200,000 Daltons.

In another embodiment, the invention provides a dried hydrogel formed by a process comprising the steps of:
  a) combining in a solvent (i) at least one polyglycerol aldehyde having aldehyde groups, said polyglycerol aldehyde having a number-average molecular weight of about 400 to about 20,000 Daltons and an equivalent weight per aldehyde group of about 100 to about 3,000 Daltons; with (ii) at least one water-dispersible, multi-arm amine, wherein at least three of the arms are terminated by at least one primary amine group, said multi-arm amine having a number-average molecular weight of about 450 to about 200,000 Daltons, to form a hydrogel; and
  b) treating said hydrogel to remove at least a portion of said solvent to form the dried hydrogel.

In another embodiment the invention provides a composition comprising the reaction product of:
  a) at least one polyglycerol aldehyde having aldehyde groups, said polyglycerol aldehyde having a number-average molecular weight of about 400 to about 20,000 Daltons and an equivalent weight per aldehyde group of about 100 to about 3,000 Daltons; and
  b) at least one water-dispersible, multi-arm amine wherein at least three of the arms are terminated by at least one primary amine group, said multi-arm amine having a number-average molecular weight of about 450 to about 200,000 Daltons.

In another embodiment, the invention provides a crosslinked hydrogel composition comprising:
  a) at least one polyglycerol aldehyde having aldehyde groups, said polyglycerol aldehyde having a number-average molecular weight of about 400 to about 20,000 Daltons and an equivalent weight per aldehyde group of about 100 to about 3,000 Daltons; and
  b) at least one water-dispersible, multi-arm amine wherein at least three of the arms are terminated by at least one primary amine group, said multi-arm amine having a number-average molecular weight of about 450 to about 200,000 Daltons;

wherein said at least one polyglycerol aldehyde and said at least one water-dispersible, multi-arm amine are crosslinked through covalent bonds formed between the aldehyde groups of the polyglycerol aldehyde and the primary amine groups of the water-dispersible, multi-arm amine.

In another embodiment, the invention provides a method for applying a coating to an anatomical site on tissue of a living organism comprising: applying to the site a) at least one polyglycerol aldehyde having aldehyde groups, said polyglycerol aldehyde having a number-average molecular weight of about 400 to about 20,000 Daltons and an equivalent weight per aldehyde group of about 100 to about 3,000 Daltons; followed by b) at least one water-dispersible, multi-arm amine wherein at least three of the arms are terminated by a primary amine group, said multi-arm amine having a number-average molecular weight of about 450 to about 200,000 Daltons, or (b) followed by (a), or premixing (a) and (b) and applying the resulting mixture to the site before the resulting mixture completely cures.

DETAILED DESCRIPTION

As used above and throughout the description of the invention, the following terms, unless otherwise indicated, shall be defined as follows:

The term "polyglycerol aldehyde" as used herein refers to a polymer that comprises glycerol monomers connected by ether linkages and having 3 to about 170 aldehyde groups per molecule.

The term "ether linkage" refers to a chemical linkage of two substituted or unsubstituted alkyl or aryl groups through an oxygen atom, (i.e., R—O—R'), is such that neither R nor R' contain another oxygen atom attached directly to the carbon atom that forms the ether linkage. That is, the ether linkage is not part of an acetal, ketal, glycosidic, ester or orthoester moiety.

The term "equivalent weight per aldehyde group", also referred to herein as "EW", refers to the molecular weight of the polyglycerol aldehyde divided by the number of aldehyde groups introduced in the molecule.

The term "m·n" means the quantity represented by "m" multiplied by the quantity represented by "n".

The term "water-dispersible, multi-arm amine" refers to a polymer having three or more polymer chains ("arms"), which may be linear or branched, emanating from a central structure, which may be a single atom, a core molecule, or a polymer backbone, wherein at least three of the branches ("arms") are terminated by at least one primary amine group. The water-dispersible, multi-arm amine is water soluble or is able to be dispersed in water to form a colloidal suspension capable of reacting with a second reactant in aqueous solution or dispersion.

The term "water-dispersible, multi-arm polyether amine" refers to a water-dispersible, multi-arm amine wherein the polymer is a polyether.

The term "polyether" refers to a polymer having the repeat unit [—O—R]—, wherein R is a hydrocarbylene group having 2 to 5 carbon atoms. The polyether may also be a random or block copolymer comprising different repeat units which contain different R groups.

The term "branched polyether" refers to a polyether having one or more branch points ("arms"), including star, dendritic, comb, and hyperbranched polyethers.

The term "dendritic polyether" refers to a highly branched polyether having a tree-like structure and a degree of branching as defined by D. Hölter, et al. (*Acta Polym.* 48:30-35, 1997) of 99.9-100% (U.S. Patent Application Publication No. 2008/0045668).

The term "comb polyether" refers to a polyether having a main chain with multiple trifunctional branch points from each of which a linear arm emanates.

The term "star polyether" refers to a polyether having a central branch point, which may be a single atom or a chemical group, from which linear arms emanate.

The term "degree of branching" is defined by D. Hölter, et al. (*Acta Polym.* 48:30-35, 1997) and refers to the percent of branch points in a polymer, relative to the maximum number of branch points theoretically possible.

The term "hyperbranched" refers to a polymer that is highly branched, having a degree of branching as defined by D. Hölter, et al. (*Acta Polym.* 48:30-35, 1997) of about 10% to about 99.9%, more particularly about 20% to about 99%, and more particularly about 30% to about 70% (U.S. Patent Application Publication No. 2008/0045668).

The term "primary amine" refers to a neutral amino group having two free hydrogens. The amino group may be bound to a primary, secondary or tertiary carbon.

The term "multi-functional amine" refers to a chemical compound comprising at least two functional groups, at least one of which is a primary amine group.

The term "crosslink" refers to a bond or chain of atoms attached between and linking two different polymer chains.

The term "crosslink density" is herein defined as the reciprocal of the average number of chain atoms between crosslink connection sites.

The term "% by weight", also referred to herein as "wt %" refers to the weight percent relative to the total weight of the solution or dispersion, unless otherwise specified.

The term "anatomical site" refers to any external or internal part of the body of humans or animals.

The term "tissue" refers to any biological tissue, both living and dead, in humans or animals.

The term "hydrogel" refers to a water-swellable polymeric matrix, consisting of a three-dimensional network of macromolecules held together by covalent crosslinks, that can absorb a substantial amount of water to form an elastic gel.

The term "PEG" as used herein refers to poly(ethylene glycol).

The term "$M_w$" as used herein refers to the weight-average molecular weight.

The term "$M_n$" as used herein refers to the number-average molecular weight.

The term "medical application" as used herein refers to medical applications as related to humans and animals.

The term "imine bond" refers to the carbon-nitrogen double bond depicted between the carbon atom labeled "C" and $NHR^5$ in structure I below, in which $R^4$ and $R^5$ are each independently unsubstituted or substituted hydrocarbyl groups. An "aminal bond" is either of the carbon-nitrogen single bonds depicted between the carbon atom labeled "C" and $NHR^7$ or $NHR^8$ in structure II, in which $R^6$, $R^7$ and $R^8$ are each independently unsubstituted or substituted hydrocarbyl groups. A "hemiaminal bond" is the carbon-nitrogen single bond depicted between the carbon atom labeled "C" and $NHR^{10}$ in structure III, in which $R^9$ and $R^{10}$ are each independently unsubstituted or substituted hydrocarbyl groups.

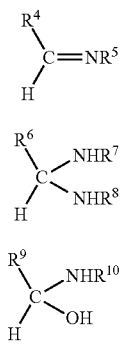

The meaning of abbreviations used is as follows: "min" means minute(s), "h" means hour(s), "sec" means second(s), "d" means day(s), "mL" means milliliter(s), "L" means liter(s), "μL" means microliter(s), "cm" means centimeter(s), "mm" means millimeter(s), "μm" means micrometer(s), "mol" means mole(s), "mmol" means millimole(s), "g" means gram(s), "mg" means milligram(s), "wt %" means percent by weight, "mol %" means mole percent, "Vol" means volume, "v/v" means volume per volume, "w/w" means weight per weight, "Da" means Dalton(s), "kDa" means kiloDalton(s), the designation "10K" means that a polymer molecule possesses a number-average molecular weight of 10 kiloDaltons, "M" means molarity, "kPa" means kilopascal(s), "NMR" means nuclear magnetic resonance spectroscopy, "$^1$H NMR" means proton nuclear magnetic resonance spectroscopy, "$^{13}$C NMR" means carbon-13 nuclear magnetic resonance spectroscopy, "ppm" means parts per million, "PBS" means phosphate-buffered saline, "MWCO" means molecular weight cut off, "psi" means pounds per square inch, "MW" means molecular weight, "FW" means formula weight, "MHz" means megahertz, "SEC" means size exclusion chromatography, "dn/dc" means the specific refractive index increment (i.e., the change in refractive index per change in concentration), "cP" means centipoise.

Disclosed herein is a hydrogel tissue adhesive and sealant formed by reacting a polyglycerol aldehyde with a water-dispersible, multi-arm amine. The polyglycerol aldehyde is more stable in aqueous solution than are oxidized polysaccharides, thereby making the tissue adhesive more practical for commercial use. The hydrogel tissue adhesive and sealant may be useful for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and preventing post-surgical adhesions.

Polyglycerol Aldehydes

Polyglycerol aldehydes are polymers that comprise glycerol monomers connected by ether linkages and having 3 to about 170 aldehyde groups per molecule. Useful polyglycerol aldehydes have number-average molecular weights of about 400 to about 20,000 Daltons, more particularly about 1,000 to about 20,000 Daltons, more particularly about 2,000 to about 20,000 Daltons, and more particularly about 2,000 to about 10,000 Daltons; and an equivalent weight per aldehyde group of about 100 to about 3,000 Daltons, more particularly about 100 to about 2,000 Daltons, more particularly about 100 to about 1,500 Daltons, more particularly about 200 to about 1,500 Daltons, more particularly about 100 to about 1,000 Daltons, more particularly about 100 to about 800 Daltons, more particularly about 200 to about 800 Daltons, and more particularly about 200 to about 400 Daltons.

In one embodiment, the polyglycerol aldehydes have the general formula:

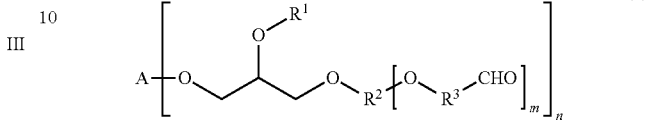

wherein: A is either (a) a hydrocarbyl group derived by removing one or more hydroxyl groups from an alcohol or polyol containing 1 to 20 carbon atoms and 1 to 8 hydroxyl groups or (b) an oxahydrocarbyl or polyoxahydrocarbyl group derived by removing one or more hydroxyl groups from the reaction product of (i) an alcohol or polyol containing 1 to 20 carbon atoms and 1 to 8 hydroxyl groups and (ii) one or more cyclic ethers such as oxirane, methyloxirane, oxetane or oxolane, wherein the $M_n$ of the reaction product is equal to or less than 5,000 Da; $R^1$ is a hydrogen atom, a 1 to 8-carbon hydrocarbyl group, $R^2$—O—[$R^3$—CHO]$_p$, or $R^3$—CHO; $R^2$ is a polymeric segment comprising 1 to 270 glycerol units connected by ether linkages; $R^3$ is a hydrocarbylene group containing 1 to 8 carbon atoms; n=1 to 8; m·n=3 to 170; and p=1 to 40. $R^2$ may also comprise other monomers including, but not limited to, oxirane, methyloxirane, oxetane and oxolane.

In one embodiment, A in general formula (1) is CH$_3$CH$_2$C(CH$_2$—)$_3$, derived by removing the three hydroxyl groups from trimethylolpropane; $R^2$ is a polymeric segment consisting of 1 to 60 glycerol units connected by ether linkages; $R^3$ is —CH$_2$—; $R^1$ is a hydrogen atom, $R^2$—O—[$R^3$—CHO]$_p$, or $R^3$—CHO; m=1 to 30; n=3; and p=1 to 30.

Polyglycerol aldehydes may be prepared from polyglycerols, which are available commercially from companies such as Hyperpolymers GmbH, Freiburg, Germany. Additionally, suitable polyglycerols may be prepared using methods known in the art such as those described by Sunder et al. (*Macromolecules* 32:4240-4246, 1999); U.S. Pat. Nos. 6,765,082 and 6,822,068, and U.S. Patent Application Publication No. 2003/0120022. Typically, polyglycerols are a heterogeneous mixture having a distribution of different molecular weights, and are characterized by an average molecular weight, for example, the weight-average molecular weight ($M_w$), or the number average molecular weight ($M_n$), as is known in the art. Suitable polyglycerols have a number-average molecular weight of about 400 to about 20,000 Daltons, more particularly about 1,000 to about 20,000 Daltons, more particularly about 2,000 to about 20,000 Daltons, and more particularly about 2,000 to about 10,000 Daltons.

The core of the polyglycerol, represented by A in general formula (1) above, may be derived from an alcohol or polyol. Examples of suitable alcohols include, but are not limited to, methanol, ethanol, propanol, isopropanol, butanol, tert-butanol, 2-methoxyethanol, 2-(2-methoxyethoxy)ethanol and monomethyl ethers of poly(ethylene glycol) and poly(propylene glycol). Examples of suitable polyols include, but are not limited to, ethylene glycol, propylene glycol, 1,2-butanediol, 1,4-butanediol, glycerol, trimethylolpropane, diglycerol, pentaerythritol, triglycerol, tetraglycerol, dipentaerythritol, sorbitol, mannitol and hexaglycerol. In addition, the core of the polyglycerol, represented by A in general formula (1), may be derived from an alcohol or polyol that has been ethoxylated, propoxylated or otherwise alkoxylated by reaction with one or more cyclic ether such as oxirane, methyloxirane, oxetane or oxolane. Ethoxylated and propoxylated alcohols and polyols are commercially available and methods for making them are well known in the art. They are sold, for example, by the Aldrich Chemical Company, Perstorp Polyols, Inc. (Toledo, Ohio), Spectrum Chemicals (Gardena, Calif.) and Wako Pure Chemical Industries (Osaka, Japan). They can be made according to methods disclosed in, for example, U.S. Patent Application Publications 2004/0096507 and 2006/0135391 and International Patent Application Publications WO 1986/002635, EP 0395316, WO 2003/027054 and WO 2006/106122. Alcohols and polyols that have been both ethoxylated and propoxylated by either random or block copolymerization are commercially available and methods for making them are well known in the art. They are sold, for example, by the Aldrich Chemical Company. They can be made according to methods disclosed in, for example, International Patent Application Publication WO 2004/076528.

Polyglycerol aldehydes may also be prepared from polyglycerols containing other epoxide monomers including but not limited to oxirane and methyloxirane. Polyglycerols containing other epoxide monomers can be prepared according to methods known in the art, such as those described in U.S. Pat. No. 6,765,082.

Polyglycerol aldehydes may be prepared by oxidizing suitable polyglycerols, which are described above, to introduce aldehyde groups using any suitable oxidizing agent, including, but not limited to, periodic acid, soluble or insoluble periodate salts, polymer-bound periodate, periodate salts adsorbed onto an insoluble carrier such as silica gel, lead tetraacetate, catalytic triphenylbismuth with N-bromosuccinimide or bromine and potassium carbonate (D. H. R. Barton et al. *Tetrahedron* 42:5627-5636, 1986; WO 2004/087634), N-iodosuccinimide, and oxygen with a catalyst such as dichlorotris(triphenylphosphine)ruthenium(II). For example, the polyglycerol may be oxidized by reaction with sodium periodate, as described in detail in the Examples herein below. The polyglycerol may be reacted with different amounts of periodate to give polyglycerol aldehydes with different degrees of oxidation and therefore, different amounts of aldehyde groups (i.e., different equivalent weights per aldehyde group). The degree of oxidation of the polyglycerol aldehyde may be determined using methods known in the art. For example, the density of aldehyde groups (mole equivalents per gram) may be determined spectrophotometrically (M. Sugimoto et al. WO 9901480) or by titration with silver oxide and potassium thiocyanate (J. A. Mayes et al. *Analytical. Chemistry* 36:934-935, 1964), sodium bisulfite and alkali (S. Siggia et al. *Analytical. Chemistry* 19:1023-1025, 1947) or hydroxylamine hydrochloride and alkali (H. Zhao et al. *Pharmaceutical Research* 8:400-402, 1991). Alternatively, the degree of oxidation of the polyglycerol aldehyde may be determined using nuclear magnetic resonance (NMR) spectroscopy.

Polyglycerol aldehydes may also be prepared by chemically modifying a suitable polyglycerol to append aldehyde groups covalently to the polymer using methods known in the art. For example, the hydroxyl groups of polyglycerol can be alkylated or acylated with compounds containing masked aldehyde groups. Examples of masked aldehyde groups include cyclic and acyclic acetals and thioacetals. Alkylating agents containing masked aldehyde groups include but are not limited to dimethyl, diethyl and other dialkyl acetals and thioacetals of 2-haloethanal, 3-halopropanal and 4-halobutanal and 2-(halomethyl)-, 2-(2-haloethyl)- and 2-(3-halopropyl) derivatives of 1,3-dioxolane, 1,3-dioxane, 1,3-dithiolane and 1,3-dithiane, wherein "halo-" is chloro, bromo or iodo. Acylating agents containing masked aldehyde groups include, but are not limited to, 3,3-dimethoxypropionyl chloride, 2-(1,3-dioxolan-2-yl)-, 2-(1,3-dioxan-2-yl)-, 2-(1,3-dithiolan-2-yl)-, and 2-(1,3-dithian-2-yl)acetyl chloride, and 3-(1,3-dioxolan-2-yl)-, 3-(1,3-dioxan-2-yl)-, 3-(1,3-dithiolan-2-yl)-, and 3-(1,3-dithian-2-yl)propionyl chloride. Once glycerol has been alkylated or acylated with a compound containing a masked aldehyde group, the aldehyde group can be unmasked by, for example, by mild acid- or metal-catalyzed hydrolysis of the acetal or thioacetal.

The hydroxyl groups of polyglycerol can also be alkylated or acylated with compounds containing functional groups that can be subsequently oxidized or reduced to aldehydes. Examples of functional groups that can be oxidized to aldehydes are carbon-carbon double bonds and primary alcohols. Examples of functional groups that can be reduced to aldehydes are carboxylic acids and esters.

Carbon-carbon double bonds can be oxidized to aldehydes by, for example, ozonolysis, dihydroxylation followed by glycol cleavage, and epoxidation followed by hydrolysis. Dihydroxylation of carbon-carbon double bonds can be achieved using, for example, osmium tetroxide, an osmate salt such as potassium osmate, or a permanganate salt such as potassium permanganate. The resulting glycols can be cleaved using, for example, periodic acid, a periodate salt such as sodium or potassium periodate, lead tetraacetate, catalytic triphenylbismuth with N-bromosuccinimide, N-iodosuccinimide or bromine, or oxygen with a catalyst such as dichlorotris(triphenylphosphine)ruthenium(II). Carbon-carbon double bonds can be epoxidized using hydrogen peroxide, alkyl peroxides such as tert-butyl peroxide, peroxycarboxylic acids such as meta-chloroperbenzoic acid, performic acid, peracetic acid, monoperoxyphthalic acid and magnesium monoperoxyphthalate, dioxiranes such as dimethyldioxirane and bis(trifluoromethyl)dioxirane, dioxygen with a suitable catalyst, iodosylbenzene, hypochlorous acid, a hypochlorite salt such as sodium hypochlorite, or potassium peroxysulfate.

Primary alcohols can be oxidized to aldehydes using, for example, pyridinium chlorochromate, dichromate salts such as sodium, potassium and pyridinium dichromate, (diacetoxyiodo)benzene, Dess-Martin periodinane, or a system in which dimethyl sulfoxide (DMSO) is the ultimate oxidant, as in the Swern and Pfitzner-Moffatt oxidations. One skilled in the art recognizes that, at the time that polyglycerol is alkylated or acylated with a compound containing a primary hydroxyl group, the hydroxyl group may be masked or "protected" using any of a variety of groups known in the art, including, but not limited to, those described by Wuts and Greene (*Greene's Protective Groups in Organic Synthesis*, 4th Edition; Wiley, 2006; chapter 2). In particular, primary hydroxyl groups may be masked as benzyl or substituted benzyl ethers, tert-butyl ethers, silyl ethers, or tetrahydropyranyl ethers.

Carboxylic acids can be reduced to aldehydes using, for example, lithium tris-tert-butoxyaluminium hydride, diisobutylaluminum hydride (DIBAL-H), thexylchloroborane-dimethylsulfide, 9-borabicyclo[3.3.1]nonane, or sodium hypophosphite and pivalic anhydride with palladium acetate-tricyclohexylphosphine as catalyst. Carboxylic esters can be reduced to aldehydes using, for example, DIBAL-H. Alternately, carboxylic esters can be reduced to the corresponding primary alcohol using, for example, lithium aluminum hydride, lithium borohydride, a lithium aminoborohydride such as lithium diethylaminoborohydride, zinc borohydride or sodium borohydride and then oxidized back up to the aldehyde as described above.

Examples of reagents that can be used to attach carbon-carbon double bonds to polyglycerol include, but are not limited to, allyl chloride, allyl bromide, allyl iodide, 3-butenyl chloride, 3-butenyl bromide, 3-butenyl iodide, allyl glycidyl ether, 4-pentenoyl chloride and allyl isocyanate. Examples of reagents that can be used to attach masked primary alcohols onto polyglycerol include, but are not limited to, 2-(trimethylsiloxy)ethyl isocyanate, 2-benzyloxyethyl isocyanate, 2-(benzyloxy)ethyl chloroformate, 2-(2-(benzyloxy)ethoxy)ethyl chloroformate, (2-benzyloxyethoxy)acetyl chloride, 1-benzyloxy-2-chloromethoxyethane. Examples of reagents that can be used to attach carboxylic acids or esters to polyglycerol include, but are not limited to, chloroacetic acid, bromoacetic acid, iodoacetic acid, methyl or ethyl chloroacetate, methyl or ethyl bromoacetate, methyl or ethyl iodoacetate, ethyl isocyanatoacetate and ethoxycarbonylmethyl chloroformate.

The amount of aldehyde groups incorporated into the polyglycerol may be determined using the methods described above.

In one embodiment, the polyglycerol aldehyde is hyperbranched, having a degree of branching of about 10% to about 99.9%, more particularly about 20% to about 99%, and more particularly about 30% to about 70%. Degree of branching may be determined by any of various methods known in the art, including but not limited to NMR spectroscopic methods. The degree of branching of a polyglycerol aldehyde may be determined by measuring the degree of branching of its precursor polyglycerol, before the precursor polyglycerol is oxidized or chemically modified, as described above, to introduce aldehyde groups, since oxidation and chemical modification of polyglycerol as described above does not alter the degree of branching of the polymer.

A method for determining the degree of branching of polyglycerols by $^{13}$C NMR spectroscopy has been described by A. Sunder et al. (*Macromolecules* 32:4240-4246, 1999). Alternatively, the degree of branching of a polyglycerol can be calculated from its number average molecular weight ($M_n$) and its equivalent weight per terminal diol moiety. The number average molecular weight can be determined by methods known in the art, including but not limited to SEC and NMR spectroscopy. The equivalent weight per terminal diol moiety can be determined, for example, by exhaustively oxidizing the diol moieties with sodium periodate and then titrating the resulting reaction solution for sodium iodate and residual sodium periodate, using a method such as, for example, that of R. Belcher et al. (*Analytica Chimica Acta* 41:395-397, 1968). For a given $M_n$, the theoretical equivalent weight per terminal diol moiety for several degrees of branching can be calculated to make a plot of degree of branching versus equivalent weight per terminal diol moiety. The curve that best fits the calculated points may be determined using nonlinear regression, and the resulting nonlinear regression equation may be used to calculate the degree of branching based on the $M_n$ and the equivalent weight per terminal diol moiety of the polyglycerol of interest, determined as described above.

Water-Dispersible, Multi-Arm Amines

Suitable water dispersible, multi-arm amines include, but are not limited to, water dispersible multi-arm polyether amines, amino-terminated dendritic polyamidoamines, and multi-arm branched end amines. Typically, the multi-arm amines have a number-average molecular weight of about 450 to about 200,000 Daltons, more particularly from about 2,000 to about 40,000 Daltons.

In one embodiment, the water dispersible, multi-arm amine is a multi-arm polyether amine, which is a water-dispersible polyether having the repeat unit [—O—R]—, wherein R is a hydrocarbylene group having 2 to 5 carbon atoms. The term "hydrocarbylene group" refers to a divalent group formed by removing two hydrogen atoms, one from each of two different carbon atoms, from a hydrocarbon. Suitable multi-arm polyether amines include, but are not limited to, amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines, sold under the trade name Jeffamine® triamines, by Huntsman LLC. (Houston, Tex.). Examples of star polyethylene oxide amines, include, but are not limited to, various multi-arm polyethylene glycol amines, and star polyethylene glycols having 3, 4, 6, or 8 arms terminated with primary amines (referred to herein as 3, 4, 6, or 8-arm star PEG amines, respectively). Examples of suitable Jeffamine® triamines include, but are not limited to, Jeffamine® T-403 (CAS No. 39423-51-3), Jeffamine® T-3000 (CAS No. 64852-22-8), and Jeffamine® T-5000 (CAS No. 64852-22-8). In one embodiment, the water-dispersible, multi-arm polyether amine is an eight-arm polyethylene glycol having eight arms terminated by a primary amine group and having a number-average molecular weight of about 10,000 Daltons.

The multi-arm polyether amines are either available commercially, as noted above, or may be prepared using methods known in the art. For example, multi-arm polyethylene glycols, wherein at least three of the arms are terminated by a primary amine group, may be prepared by putting amine ends on multi-arm polyethylene glycols (e.g., 3, 4, 6, and 8-arm star polyethylene glycols, available from companies such as Nektar Transforming Therapeutics; SunBio, Inc., Anyang City, South Korea; NOF Corp., Tokyo, Japan; or JenKem Technology USA, Allen, Tex.) using the method described by Buckmann et al. (*Makromol. Chem.* 182:1379-1384, 1981). In that method, the multi-arm polyethylene glycol is reacted with thionyl bromide to convert the hydroxyl groups to bromines, which are then converted to amines by reaction with ammonia at 100° C. The method is broadly applicable to the preparation of other multi-arm polyether amines. Additionally, multi-arm polyether amines may be prepared from multi-arm polyols using the method described by Chenault (copending and commonly owned U.S. Patent Application Publication No. 2007/0249870). In that method, the multi-arm polyether is reacted with thionyl chloride to convert the hydroxyl groups to chlorine groups, which are then converted to amines by reaction with aqueous or anhydrous ammonia. Other methods that may be used for preparing multi-arm polyether amines are described by Merrill et al. in U.S. Pat. No. 5,830,986, and by Chang et al. in WO 97/30103.

The water-dispersible, multi-arm amine may also be an amino-terminated dendritic polyamidoamine, sold under the trade name Starburst® Dendrimers (available from Sigma-Aldrich, St Louis, Mo.).

In one embodiment, the water-dispersible, multi-arm amine is a multi-arm branched end amine, as described by Arthur (copending and commonly owned International Patent Application Publication No. WO 2008/066787). The multi-arm branched end amines are branched polymers having two or three amine groups at the end of the polymer arms. The multiplicity of functional groups increases the statistical probability of reaction at a given chain end and allows more efficient incorporation of the branched molecules into a polymer network. The starting materials used to prepare the branched end amines may be branched polymers such as multi-arm polyether polyols including, but not limited to, comb and star polyether polyols. The branched end amines can be prepared by attaching multiple amine groups to the ends of the polymer by reaction with the hydroxyl groups using methods well known in the art. For example, a branched end amine having two amine functional groups on each end of the polymer arms can be prepared by reacting the starting material, as listed above, with thionyl chloride in a suitable solvent such as toluene to give the chloride derivative, which is subsequently reacted with tris(2-aminoethyl)amine to give the branched end reactant having two primary amine groups at the end of the polymer arms.

It should be recognized that the water-dispersible, multi-arm amines are generally a somewhat heterogeneous mixture having a distribution of arm lengths and, in some cases, a distribution of species with different numbers of arms. When a multi-arm amine has a distribution of species having different numbers of arms, it can be referred to based on the average number of arms in the distribution. For example, in one embodiment, the multi-arm amine is an 8-arm star PEG amine, which comprises a mixture of multi-arm star PEG amines, some having less than and some having more than 8 arms; however, the multi-arm star PEG amines in the mixture have an average of 8 arms. Therefore, the terms "8-arm", "6-arm", "4-arm" and "3-arm" as used herein to refer to multi-arm amines, should be construed as referring to a heterogeneous mixture having a distribution of arm lengths and, in some cases, a distribution of species with different numbers of arms, in which case the number of arms recited refers to the average number of arms in the mixture.

Methods of Using the Hydrogel Tissue Adhesive

The hydrogel tissue adhesive disclosed herein may be used in various forms. In one embodiment, the polyglycerol aldehyde and the water-dispersible, multi-arm amine are used in the form of aqueous solutions or dispersions. Dispersion, as used herein, refers to a colloidal suspension capable of reacting with a second reactant in an aqueous medium. To prepare an aqueous solution or dispersion comprising a polyglycerol aldehyde (referred to herein as the "first aqueous solution or dispersion"), at least one polyglycerol aldehyde is added to water to give a concentration of about 5% to about 40%, more particularly from about 5% to about 30%, more particularly from about 10% to about 30%, and more particularly from about 20% to about 30% by weight relative to the total weight of the solution or dispersion. Additionally, a mixture of at least two different polyglycerol aldehydes having different weight-average molecular weights, different degrees of aldehyde substitution (i.e., different equivalent weights per aldehyde group), or both different weight-average molecular weights and degrees of aldehyde substitution may be used. Where a mixture of polyglycerol aldehydes is used, the total concentration of the polyglycerol aldehydes is about 5% to about 40% by weight, more particularly from about 5% to about 30%, more particularly from about 10% to about 30%, and more particularly from about 20% to about 30% by weight relative to the total weight of the solution or dispersion.

Similarly, to prepare an aqueous solution or dispersion comprising a water-dispersible, multi-arm amine (referred to herein as the "second aqueous solution or dispersion"), at least one water-dispersible, multi-arm amine is added to water to give a concentration of about 5% to about 70%, more particularly from about 10% to about 50%, more particularly from about 20% to about 50%, and more particularly from about 20% to about 30% by weight relative to the total weight of the solution or dispersion. The optimal concentration to be used depends on the intended application and on the concentration of the polyglycerol aldehyde used in the first aqueous solution or dispersion. Additionally, a mixture of different water-dispersible, multi-arm amines having different number-average molecular weights, different numbers of arms, or both different number-average molecular weights and different numbers of arms may be used. Where a mixture of water-dispersible, multi-arm amines is used, the total concentration of the multi-arm amines is about 5% to about 70%, more particularly from about 10% to about 50%, more particularly from about 20% to about 50%, and more particularly from about 20% to about 30% by weight relative to the total weight of the solution or dispersion.

For use on living tissue, it is preferred that the first aqueous solution or dispersion and the second aqueous solution or dispersion be sterilized to prevent infection. Any suitable sterilization method known in the art that does not adversely affect the ability of the components to react to form an effective hydrogel may be used, including, but not limited to, electron beam irradiation, gamma irradiation, ethylene oxide sterilization, or ultra-filtration through a 0.2 μm pore membrane.

The first aqueous solution or dispersion and the second aqueous solution or dispersion may further comprise various additives depending on the intended application. Preferably, the additive does not interfere with effective gelation to form a hydrogel. The amount of the additive used depends on the particular application and may be readily determined by one skilled in the art using routine experimentation. For example, the first aqueous solution or dispersion and/or the second aqueous solution or dispersion may comprise at least one additive selected from pH modifiers, viscosity modifiers, anti-oxidants, stabilizers, antimicrobials, colorants, surfactants, additives that increase or decrease the rate of degradation of the hydrogel tissue adhesive or sealant, pharmaceutical drugs and therapeutic agents.

The first aqueous solution or dispersion and/or the second aqueous solution or dispersion may optionally include at least one pH modifier to adjust the pH of the solution(s) or dispersion(s). Suitable pH modifiers are well known in the art. The pH modifier may be an acidic or basic compound. Examples of acidic pH modifiers include, but are not limited to, carboxylic acids, inorganic acids, and sulfonic acids. Examples of basic pH modifiers include, but are not limited to, hydroxides, alkoxides, carboxylates, nitrogen-containing compounds other than primary and secondary amines, and basic carbonates and phosphates.

The first aqueous solution or dispersion and/or the second aqueous solution or dispersion may optionally include at least one antimicrobial agent. Suitable antimicrobial preservatives are well known in the art. Examples of suitable antimicrobials include, but are not limited to, alkyl parabens, such as methylparaben, ethylparaben, propylparaben, and butylparaben; triclosan; chlorhexidine; cresol; chlorocresol; hydroquinone; sodium benzoate and potassium benzoate; polyhexamethylene biguanide; antibiotics effective against bacteria, including aminoglycoside antibiotics such as gentamicin, streptomycin, amikacin and kanamycin, a cephalosporin such as cephalexin and cephtriaxone, a carbacephem such as loracarbef, a glycopeptide such as vancomycin, a macrolide such as erythromycin and rifampicin, a penicillin such as amoxicillin and ampicillin, a polypeptide such as bacitracin and polymyxin B, a quinolone such as ciprofloxacin, levofloxacin and moxifloxacin, a tetracycline such as oxytetracycline and doxycycline, and a sulfonamide; antifungals such as ketoconazole, miconazole and amphotericin B; antivirals such as acyclovir or AZT; antihelminthics; and antiprotozoals.

The first aqueous solution or dispersion and/or the second aqueous solution or dispersion may optionally include at least one colorant to enhance the visibility of the solution(s) or dispersion(s). Suitable colorants include dyes, pigments, and natural coloring agents. Examples of suitable colorants include, but are not limited to, FD&C and D&C colorants, such as FD&C Violet No. 2, FD&C Blue No. 1, D&C Green No. 6, D&C Green No. 5, D&C Violet No. 2; and natural colorants such as beetroot red, canthaxanthin, chlorophyll, eosin, saffron, and carmine.

The first aqueous solution or dispersion and/or the second aqueous solution or dispersion may optionally include at least one surfactant. Surfactant, as used herein, refers to a compound that lowers the surface tension of water. The surfactant may be an ionic surfactant, such as sodium lauryl sulfate, or a neutral surfactant, such as polyoxyethylene ethers, polyoxyethylene esters, and polyoxyethylene sorbitan.

Additionally, the first aqueous solution or dispersion and/or the second aqueous solution or dispersion may optionally include at least one pharmaceutical drug or therapeutic agent. Suitable drugs and therapeutic to agents are well known in the art (for example see the United States Pharmacopeia (USP), Physician's Desk Reference (Thomson Publishing), The Merck Manual of Diagnosis and Therapy 18th ed., Mark H. Beers and Robert Berkow (eds.), Merck Publishing Group, 2006; or, in the case of animals, The Merck Veterinary Manual, 9th ed., Kahn, C. A. (ed.), Merck Publishing Group, 2005). Nonlimiting examples include anti-inflammatory agents, for example, glucocorticoids such as prednisone, dexamethasone, budesonide; non-steroidal anti-inflammatory agents such as indomethacin, salicylic acid acetate, ibuprofen, sulindac, piroxicam, and naproxen; fibrinolytic agents such as a tissue plasminogen activator and streptokinase; anti-coagulants such as heparin, hirudin, ancrod, dicumarol, sincumar, iloprost, L-arginine, dipyramidole and other platelet function inhibitors; antibodies; nucleic acids; peptides; hormones; growth factors; cytokines; chemokines; clotting factors; endogenous clotting inhibitors; antibacterial agents; antiviral agents; antifungal agents; anti-cancer agents; cell adhesion inhibitors; healing promoters; vaccines; thrombogenic agents, such as thrombin, fibrinogen, homocysteine, and estramustine; radio-opaque compounds, such as barium sulfate and gold particles and radiolabels.

Additionally, the second aqueous solution or dispersion comprising the multi-arm amine may optionally comprise at least one other multi-functional amine having one or more primary amine groups to provide other beneficial properties, such as hydrophobicity or modified crosslink density. The multi-functional amine is capable of inducing gelation when mixed with an oxidized polysaccharide in an aqueous solution or dispersion. The multi-functional amine may be a second water dispersible, multi-arm amine, such as those described above, or another type of multi-functional amine, including, but not limited to, linear and branched diamines, such as diaminoalkanes, polyaminoalkanes, and spermine; branched polyamines, such as polyethylenimine; cyclic diamines, such as N,N'-bis(3-aminopropyl)piperazine, 5-amino-1,3,3-trimethylcyclohexanemethylamine, 1,3-bis (aminomethyl)cyclohexane, 1,4-diaminocyclohexane, and p-xylylenediamine; aminoalkyltrialkoxysilanes, such as 3-aminopropyltrimethoxysilane and 3-aminopropyltriethoxysilane; aminoalkyldialkoxyalkylsilanes, such as 3-aminopropyldiethoxymethylsilane, dihydrazides, such as adipic dihydrazide; linear polymeric diamines, such as linear polyethylenimine, $\alpha,\omega$-amino-terminated polyethers, $\alpha,\omega$-bis(3-aminopropyl)polybutanediol, $\beta,\omega$-1-amino-terminated polyethers (linear Jeffamines®); comb polyamines, such as chitosan, polyallylamine, and polylysine, and di- and polyhydrazides, such as bis(carboxyhydrazido)polyethers and poly(carboxyhydrazido) star polyethers. Many of these compounds are commercially available from companies such as Sigma-Aldrich and Huntsman LLC. Typically, if present, the multi-functional amine is used at a concentration of about 5% by weight to about 1000% by weight relative to the weight of the multi-arm amine in the aqueous solution or dispersion.

When the first aqueous solution or dispersion and the second aqueous solution or dispersion are mixed they react to form a crosslinked hydrogel comprising at least one polyglycerol aldehyde containing aldehyde groups; and at least one water-dispersible, multi-arm amine wherein at least three of the arms are terminated by at least one primary amine group, and wherein the at least one polyglycerol aldehyde and the at least one water-dispersible, multi-arm amine are crosslinked through covalent bonds formed between the aldehyde groups of the polyglycerol aldehyde and the primary amine groups of the water-dispersible, multi-arm amine. The covalent bonds may be imine, aminal, or hemiaminal bonds.

The first aqueous solution or dispersion and the second aqueous solution or dispersion may be used to apply a coating to an anatomical site on tissue of a living organism. The two aqueous solutions or dispersions may be applied to the site in any number of ways. Once both solutions or dispersions are combined on a site, they crosslink to form a hydrogel which provides a coating on the site.

In one embodiment, the two aqueous solutions or dispersions are applied to the site sequentially using any suitable means including, but not limited to, spraying, brushing with a cotton swab or brush, or extrusion using a pipette, or a syringe. The solutions or dispersions may be applied in any order. Then, the solutions or dispersions are mixed on the site using any suitable device, such as a cotton swab, a spatula, or the tip of the pipette or syringe.

In another embodiment, the two aqueous solutions or dispersions are mixed manually before application to the site. The resulting mixture is then applied to the site before it completely cures using a suitable applicator, as described above.

In another embodiment, the first aqueous solution or dispersion and the second aqueous solution or dispersion are applied to the site simultaneously where they mix to form a hydrogel. For example, the two aqueous solutions or dispersions may be contained in separate barrels of a double-barrel syringe. In this way the two aqueous solutions or dispersions are applied simultaneously to the site with the syringe. Suitable double-barrel syringe applicators are known in the art. For example, RedI describes several suitable applicators for use in the invention in U.S. Pat. No. 6,620,125, (particularly FIGS. 1, 5, and 6, which are described in Columns 4, line 10 through column 6, line 47). Additionally, the two aqueous solutions or dispersions may be applied to the site using a dual-lumen catheter, such as those available from Bistech, Inc. (Woburn, Mass.). Additionally, injection devices for introducing two liquid components endoscopically into the body simultaneously are known in the art and may be adapted for the delivery of the two aqueous solutions or dispersions disclosed herein (see for example, Linder et al., U.S. Pat. No. 5,322,510).

In another embodiment, the first aqueous solution or dispersion and the second aqueous solution or dispersion may be premixed and delivered to the site using a double barrel syringe containing a motionless mixer, such as that available from ConProtec, Inc. (Salem, N.H.) or Mixpac Systems AG (Rotkreuz, Switzerland). Alternatively, the mixing tip may be equipped with a spray head, such as that described by Cruise et al. in U.S. Pat. No. 6,458,147. Additionally, the mixture of the two aqueous solutions or dispersions from the double-barrel syringe may be applied to the site using a catheter or endoscope. Devices for mixing a two liquid component tissue adhesive and delivering the resulting mixture endoscopically are known in the art and may be adapted for the mixing and delivery of the two aqueous solutions or dispersions disclosed herein (see for example, Nielson, U.S. Pat. No. 6,723,067; and Redl et al., U.S. Pat. No. 4,631,055).

In another embodiment, the two aqueous solutions or dispersions may be applied to the site using a spray device, such as those described by Fukunaga et al. (U.S. Pat. No. 5,582,596), Delmotte et al. (U.S. Pat. No. 5,989,215) or Sawhney (U.S. Pat. No. 6,179,862).

In another embodiment, the two aqueous solutions or dispersions may be applied to the site using a minimally invasive surgical applicator, such as those described by Sawhney (U.S. Pat. No. 7,347,850).

In another embodiment, the hydrogel tissue adhesive of the invention is used to bond at least two anatomical sites together. In this embodiment, the first aqueous solution or dispersion is applied to at least one anatomical site, and the second aqueous solution or dispersion is applied to at least one of either the same site or one other site using the methods described above. The two or more sites are contacted and held together manually or using some other means, such as a surgical clamp, for a time sufficient for the mixture to cure. Alternatively, a mixture of the two aqueous solutions or dispersions is applied to at least one of the anatomical sites to be bonded using methods described above. The two or more sites are contacted and held together manually or using some other means, such as a surgical clamp, for a time sufficient for the mixture to cure.

In another embodiment, the hydrogel tissue adhesive disclosed herein may be used in the form of a dried hydrogel. In this embodiment, a dried hydrogel is prepared by combining in a solvent at least one polyglycerol aldehyde with at least one water-dispersible, multi-arm amine to form a hydrogel, and treating the hydrogel to remove at least a portion of the solvent to form the dried hydrogel. Suitable solvents include, but are not limited to, water, ethanol, isopropanol, tetrahydrofuran, hexanes, polyethylene glycol, and mixtures thereof. If two different solvents are used, the two solvents are miscible with each other. In one embodiment, the solvent is water. The polyglycerol aldehyde and the water-dispersible, multi-arm amine may be combined in various ways. For example, the first aqueous solution or dispersion comprising the polyglycerol aldehyde and the second aqueous solution or dispersion comprising the water-dispersible, multi-arm amine, may be prepared and mixed as described above to form the hydrogel. The solutions or dispersions used to prepare the dried hydrogel may further comprise various additives depending on the intended application. Any of the additives described above may be used. The hydrogel is then treated to remove at least a portion of the solvent contained therein to form the dried hydrogel. Preferably, substantially all of the solvent is removed from the hydrogel. The solvent may be removed from the hydrogel using methods known in the art, for example, using heat, vacuum, a combination of heat and vacuum, or flowing a stream of dry air or a dry inert gas such as nitrogen over the hydrogel. The dried hydrogel may be sterilized using the methods described above. The dried hydrogel may be applied to an anatomical site in a number of ways, as described below. The dried hydrogel may be hydrated on the site by the addition of a suitable aqueous solution such as water or a buffer (e.g., phosphate-buffered saline) or by the physiological fluids present at the site.

In one embodiment, the dried hydrogel may be used in the form of a film. The dried hydrogel film may be formed by casting a mixture of the solutions or dispersions on a suitable substrate and treating the resulting hydrogel to form a dried hydrogel film. The dried hydrogel film may be applied directly to an anatomical site. Additionally, the dried hydrogel film may be used to bond two anatomical sites together.

In another embodiment, the dried hydrogel may be used in the form of finely divided particles. The dried hydrogel particles may be formed by comminuting the dried hydrogel using methods known in the art, including, but not limited to, grinding, milling, or crushing with a mortar and pestle. The dried hydrogel particles may be applied to an anatomical site in a variety of ways, such as sprinkling or spraying, and may also be used to bond two anatomical sites together.

Kits

In one embodiment, the invention provides a kit comprising at least one polyglycerol aldehyde and at least one water-dispersible, multi-arm amine wherein at least three of the arms are terminated by at least one primary amine group.

In another embodiment, the kit comprises a first aqueous solution or dispersion comprising at least one polyglycerol aldehyde and a second aqueous solution or dispersion comprising at least one water-dispersible, multi-arm amine. Each of the aqueous solutions or dispersions may be contained in any suitable vessel, such as a vial or a syringe barrel.

In another embodiment, the kit comprises a dried hydrogel as described above. The dried hydrogel may be in the form of a film, finely divided particles, or other dried forms. The kit may further comprise an aqueous solution for hydrating the dried hydrogel. The dried hydrogel particles may be contained in any suitable container.

Medical Applications

The tissue adhesive and sealant disclosed herein may be useful for medical and veterinary applications, including, but not limited to, wound closure, supplementing or replacing sutures or staples in internal surgical procedures such as intestinal anastomosis and vascular anastomosis, tissue repair, preventing leakage of fluids such as blood, bile, gastrointestinal fluid and cerebrospinal fluid, ophthalmic procedures, drug delivery, and to prevent post-surgical adhesions. In these applications, the polyglycerol aldehyde and the water-dispersible, multi-arm amine, or the dried hydrogel may be applied to the desired anatomical site using the methods described above.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Reagents
Highly Branched Polyglycerols

Highly branched polyglycerols having nominal molecular weights of 500 (PG-500), 2,000 (PG-2000) and 5,000 (PG-5000) were purchased from Hyperpolymers GmbH, Freiburg, Germany. Hyperbranched polyglycerols having nominal MW 1,000, 5,000 and 10,000 were synthesized according to the method of Sunder et al. (*Macromolecules* 32:4240-4246, 1999).

Preparation of Dextran Aldehydes

Dextran aldehyde is made by oxidizing dextran in aqueous solution with sodium metaperiodate. D10-50, an oxidized dextran having an average molecular weight of about 10,000 Da and an oxidation conversion of about 50% (i.e., about half of the glucose rings in the dextran polymer are oxidized to dialdehydes) and an equivalent weight (EW) per aldehyde group of about 150, is prepared from dextran having a weight-average molecular weight of 8,500 to 11,500 Daltons (Sigma) by the method described by Cohen et al. (copending and commonly owned International Patent Application Publication No. WO 2008/133847). A typical procedure is described here.

A 20-L reactor equipped with a mechanical stirrer, addition funnel, internal temperature probe, and nitrogen purge is charged with 1000 g of the dextran and 9.00 L of de-ionized water. The mixture is stirred at ambient temperature to dissolve the dextran and then cooled to 10 to 15° C. To the cooled dextran solution is added over a period of an hour, while keeping the reaction temperature below 25° C., a solution of 1000 g of sodium periodate dissolved in 9.00 L of de-ionized water. Once all the sodium periodate solution has been added, the mixture is stirred at 20 to 25° C. for 4 more hours. The reaction mixture is then cooled to 0° C. and filtered to clarify. Calcium chloride (500 g) is added to the filtrate, and the mixture is stirred at ambient temperature for 30 min and then filtered. Potassium iodide (400 g) is added to the filtrate, and the mixture is stirred at ambient temperature for 30 min. A 3-L portion of the resulting red solution is added to 9.0 L of acetone over a period of 10 to 15 min with vigorous stirring by a mechanical stirrer during the addition. After a few more minutes of stirring, the agglomerated product is separated from the supernatant liquid. The remaining red solution obtained by addition of potassium iodide to the second filtrate is treated in the same manner as above. The combined agglomerated product is broken up into pieces, combined with 2 L of methanol in a large stainless steel blender, and blended until the solid becomes granular. The granular solid is recovered by filtration and dried under vacuum with a nitrogen purge. The granular solid is then hammer milled to a fine powder. A 20-L reactor is charged with 10.8 L of de-ionized water and 7.2 L of methanol, and the mixture is cooled to 0° C. The granular solid formed by the previous step is added to the reactor and the slurry is stirred vigorously for one hour. Stirring is discontinued, and the solid is allowed to settle to the bottom of the reactor. The supernatant liquid is decanted by vacuum, 15 L of methanol is added to the reactor, and the slurry is stirred for 30 to 45 min while cooling to 0° C. The slurry is filtered in portions, and the recovered solids are washed with methanol, combined, and dried under vacuum with a nitrogen purge to give about 600 g of the oxidized dextran, which is referred to herein as D10-50.

The degree of oxidation of the product is determined by proton NMR to be about 50% (equivalent weight per aldehyde group=150). In the NMR method, the integrals for two ranges of peaks are determined, specifically, —O$_2$CHx- at about 6.2 parts per million (ppm) to about 4.15 ppm (minus the HOD peak) and —OCHx- at about 4.15 ppm to about 2.8 ppm (minus any methanol peak if present). The calculation of oxidation level is based on the calculated ratio (R) for these areas, specifically, R=(OCH)/(O$_2$CH), i.e., $$\% \text{ oxidation} = 100 - \frac{300 \times (R-1)}{3 + 2 \times R}$$

D10-20, an oxidized dextran having an average molecular weight of about 10,000 Da, an oxidation conversion of about 20% and an EW per aldehyde group of about 400, is prepared in a manner similar to that described above but using proportionately less sodium periodate.

Preparation of Eight-Arm PEG 10K Octaamine (P8-10-1):

Eight-arm PEG 10K octaamine ($M_n$=10 kDa) is synthesized using the two-step procedure described by Chenault in co-pending and commonly owned U.S. Patent Application Publication No. 2007/0249870. In the first step, the 8-arm PEG 10K octachloride is made by reaction of thionyl chloride with the 8-arm PEG 10K octaol. In the second step, the 8-arm PEG 10K octachloride is reacted with aqueous ammonia to yield the 8-arm PEG 10K octaamine. A typical procedure is described here.

The 8-arm PEG 10K octaol ($M_n$=10000; SunBright HGEO-10000; NOF Corp., 1000 g) is dissolved in 1.5 L of toluene under an atmosphere of nitrogen in a 4-L glass reaction vessel equipped with a stirrer, reflux condenser and distillation head. The mixture is dried azeotropically by distillative removal of about 500 mL of toluene under reduced pressure (13 kPa, pot temperature 65° C.). The mixture is brought back to atmospheric pressure with nitrogen, and thionyl chloride (233 mL) is added to the mixture over 10 min, keeping the pot temperature below 85° C. After the addition of thionyl chloride is complete, the mixture is heated to 85° C. and stirred at 85° C. for 4 h. Excess thionyl chloride and most of the toluene is removed by vacuum distillation (2 kPa, pot temperature 40-60° C.). Two successive 500-mL portions of toluene are added and evaporated under reduced pressure (2 kPa, bath temperature 60° C.) to complete the removal of thionyl chloride. The pressure is reduced to 0.7–0.9 kPa, and distillation is continued with a pot temperature of 85° C. for 60-90 minutes to complete the removal of toluene. Proton NMR results from one synthesis are: $^1$H NMR (500 MHz, DMSO-d6) δ 3.71-3.69 (m, 16H), 3.67-3.65 (m, 16H), 3.50 (s, ~800H). While the product is still warm, it is dissolved in 1 L of de-ionized water and discharged from the reaction vessel.

The aqueous solution of 8-arm PEG 10K octachloride prepared above is combined with 16 L of concentrated aqueous ammonia (28 wt %) in a 5-gallon stainless steel pressure vessel equipped with a stirrer, and the atmosphere is replaced with nitrogen. The vessel is sealed, and the mixture is heated at 60° C. for 48 hours. The mixture is cooled to 40° C. and sparged with nitrogen (2 L/min) for 18-24 hours with dry nitrogen to drive off ammonia. The nitrogen flow is stopped, and the mixture is stirred under vacuum (2 kPa) for 2 hours at 40° C. The remaining solution is passed through 5.0 kg of strongly basic anion exchange resin (Purolite® A-860, The Purolite Co., Bala-Cynwyd, Pa.) in the hydroxide form packed a 30 inch-long×6 inch-outer diameter column. The eluant is collected and two 7-L portions of de-ionized water are passed through the column and also collected. The aqueous solutions are combined, concentrated under reduced pressure (2 kPa, bath temperature 60° C.) and then dried further at 60° C./0.3 kPa to give about 900-950 g of the 8-arm PEG 10K octaamine, referred to herein as P8-10-1, as a colorless waxy solid.

Preparation of Eight-Arm PEG 10K Hexadecamine (P8-10-2):

Eight-arm PEG 10K hexadecamine ($M_n$=10 kDa, average of 16 primary amine groups per polymer molecule) is synthesized using the two-step procedure described by Arthur et al. in co-pending and commonly owned Patent Application Publication No. WO 2008/066787. In the first step, the 8-arm PEG 10K octamesylate is made by reacting the 8-arm PEG 10K octaol with methanesulfonyl chloride in the presence of triethylamine. In the second step, the 8-arm PEG 10K octamesylate is reacted in water with tris(2-aminoethyl) amine to yield the 8-arm PEG 10K hexadecamine. A typical procedure is described here.

Triethylamine (8.8 mL) is added to a solution of 40 g of the 8-arm PEG 10K octaol ($M_n$=10000; SunBright HGEO-10000; NOF Corp.) in 200 mL of $CH_2Cl_2$ under a blanket of nitrogen. The mixture is cooled with stirring in an ice-water bath. Methanesulfonyl chloride (4.8 mL) is added dropwise to the stirred reaction mixture at 0° C. (CAUTION: EXOTHERM). When the addition of methanesulfonyl chloride is complete, the ice-water bath is removed, and the reaction is stirred at room temperature overnight. The reaction volume is reduced to 80 mL by rotary evaporation and transferred to a separatory funnel, where it is washed gently three times with 60 mL of 1.0 M aqueous potassium dihydrogen phosphate, once with 60 mL of 1 M aqueous potassium carbonate, and once with 60 mL of water. The $CH_2Cl_2$ layer is dried over of $MgSO_4$, filtered, and concentrated by rotary evaporation to afford a syrup. Yield 85-90%.

A solution of 30 g of 8-arm PEG 10K octamesylate in 149 mL of water is added to a solution of 149 mL of tris(2-aminoethyl)amine in 149 mL of water, and the mixture is stirred at room temperature overnight. Aqueous sodium bicarbonate (10 wt %, 150 mL) is added to the reaction mixture, which is then extracted three times with 180-mL portions of $CH_2Cl_2$. The combined organic layer is dried over $MgSO_4$, filtered, and concentrated by rotary evaporation. The resulting clear syrup is precipitated in 500 mL of ether and cooled in an ice bath. The white solid is collected by filtration and dried under high vacuum overnight. Yield 90%. The 8-arm PEG 10K hexadecamine product is referred to herein as P8-10-2.

Example 1

Synthesis of Polyglycerol Aldehyde MW 500

The purpose of this Example was to prepare a polyglycerol aldehyde having an average molecular weight of about 500 Da. The polyglycerol aldehyde was prepared by oxidizing polyglycerol having an average molecular weight of about 500 Da using sodium periodate, i.e.,

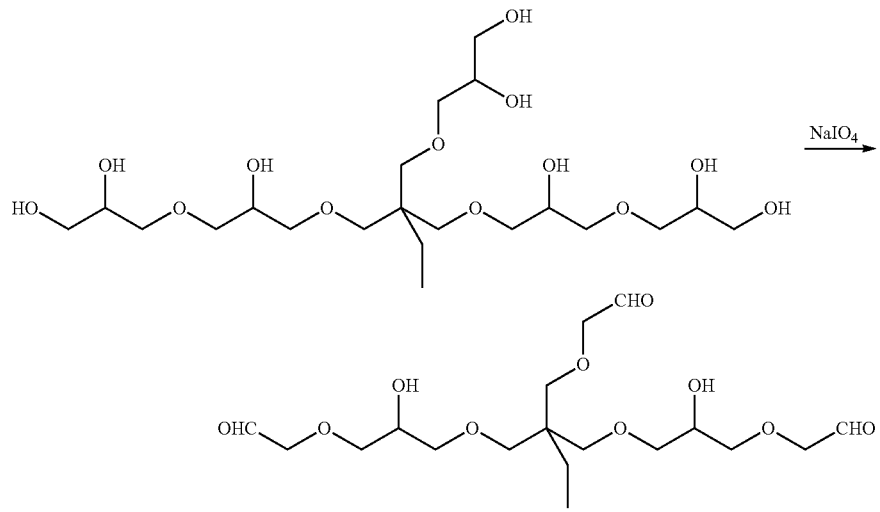

A solution of 1.90 g of sodium periodate in 15 mL of water was added to a solution of 1.00 g of polyglycerol PG-500 (Hyperpolymers GmbH, Freiburg, Germany) in 15 mL of water, slowly enough to keep the reaction temperature from rising above 30° C. Once the addition was completed, the mixture was stirred at ambient temperature for 2 hours and then poured into 75 mL of methanol. After the precipitated salts had been removed by filtration, the filtrate was evaporated under reduced pressure to give the polyglycerol aldehyde product, which was characterized using $^1$H NMR (500 MHz, methanol-$d_4$).

Example 2

Synthesis of Polyglycerol Aldehyde MW 1,000

The purpose of this Example was to prepare a polyglycerol aldehyde having an average molecular weight of about 1,000 Da. The polyglycerol aldehyde was prepared by oxidizing polyglycerol having an average molecular weight of about 1,000 Da and a degree of branching of about 48% using sodium periodate. The degree of branching of the starting polyglycerol 1000 was determined using the $^{13}$C NMR spectroscopy method described by A. Sunder et al. (*Macromolecules* 32:4240-4246, 1999).

A solution of 2.52 g of sodium periodate in 20 mL of water was added to a solution of 2.09 g of polyglycerol 1000 in 10 mL of water, slowly enough to keep the reaction temperature from rising above 30° C. Once the addition was completed, the mixture was stirred at ambient temperature for 2 hours, chilled to 0° C. and filtered to remove solids. Calcium chloride dihydrate (0.67 g) was added to the filtrate, which was stirred for 30 min and then filtered to remove solids, generating a second filtrate. To the second filtrate was added 0.5 mL of acetic acid and 3.4 g of potassium iodide. The mixture was stirred for 1 hour, diluted with 90 mL of acetone, and filtered to recover the precipitated polymer. The polymer was washed with a total of 250 mL of acetone, in portions, to remove the brown color of iodine. The polymer was dissolved in methanol, the solution was filtered and then evaporated under reduced pressure, and the residue was dried under vacuum. The yield of polyglycerol aldehyde product was 1.157 g (68%). The polyglycerol aldehyde product was characterized using $^1$H NMR (500 MHz, D$_2$O).

Example 3

Synthesis of Polyglycerol Aldehyde MW 2,000

The purpose of this Example was to prepare a polyglycerol aldehyde having an average molecular weight of about 2,000 Da. The polyglycerol aldehyde was prepared by oxidizing polyglycerol having an average molecular weight of about 2,000 Da and a degree of branching of about 51%, using sodium periodate. The degree of branching of the starting polyglycerol 2000 was determined using the $^{13}$C NMR spectroscopy method described by A. Sunder et al. (*Macromolecules* 32:4240-4246, 1999) and was also calculated from its number average molecular weight ($M_n$) and its equivalent weight per terminal diol moiety, as described above. Both methods gave comparable results.

A solution of 21.20 g of NaIO$_4$ in 193 mL of water was added to a solution of 21.95 g of polyglycerol 2000 (Hyperpolymers GmbH) dissolved in 86 mL of water, slowly enough to keep the reaction temperature from rising above 30° C. Once the addition was completed, the mixture was stirred at ambient temperature for half an hour. Titration of an aliquot of the reaction mixture for iodate and residual periodate, according to the method of Belcher et al. (*Analytica Chimica Acta* 41:395-397, 1968), indicated that 97.5% of the periodate had been consumed and converted to iodate. The reaction solution was dialyzed (Spectrum Spectrapor 6 tubing, MWCO 1,000) for 2.5 days against 6, 7-L portions of deionized water, until treating a 1-mL aliquot of the dialyzate with 2 mL of 2.1 M chloroacetate buffer, pH 2.0, a pinch of potassium iodide and 6 drops of 1% starch gave no color. The solution in the dialysis tubing was frozen and lyophilized to give the polyglycerol aldehyde MW 2,000, which was characterized using $^1$H NMR (500 MHz, D$_2$O).

Example 4

Synthesis of Polyglycerol Aldehyde MW 5,000, EW 200

The purpose of this Example was to prepare a polyglycerol aldehyde having an average molecular weight of about 5,000 Da and an equivalent weight per aldehyde group of about 200 Da. The polyglycerol aldehyde was prepared by oxidizing polyglycerol having an average molecular weight of about 5,000 Da and a degree of branching of about 60% using sodium periodate and purified by dialysis, i.e.,

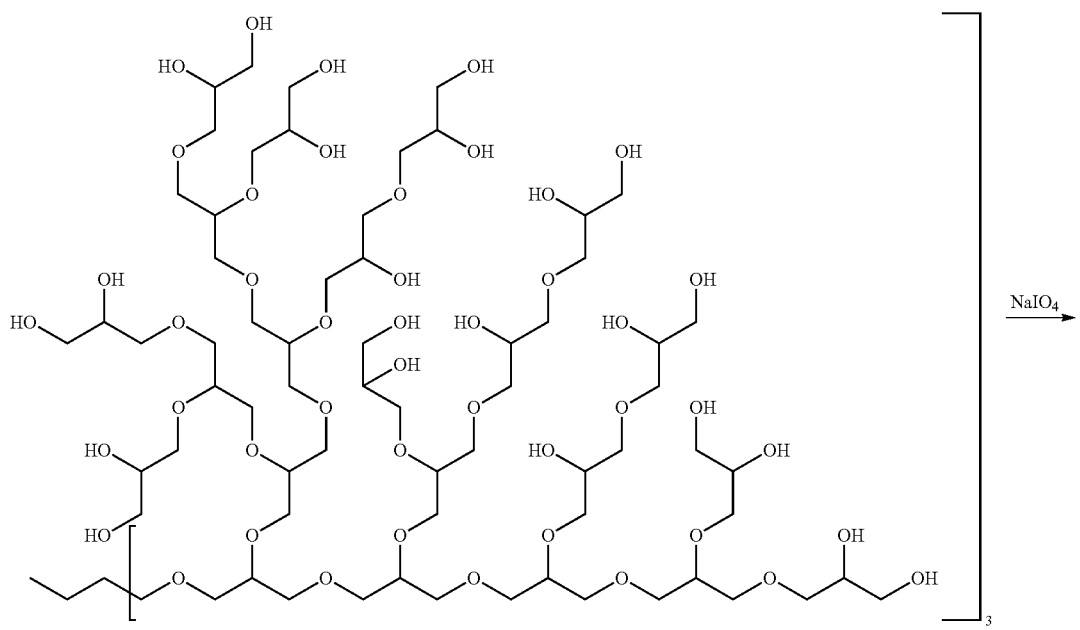

-continued

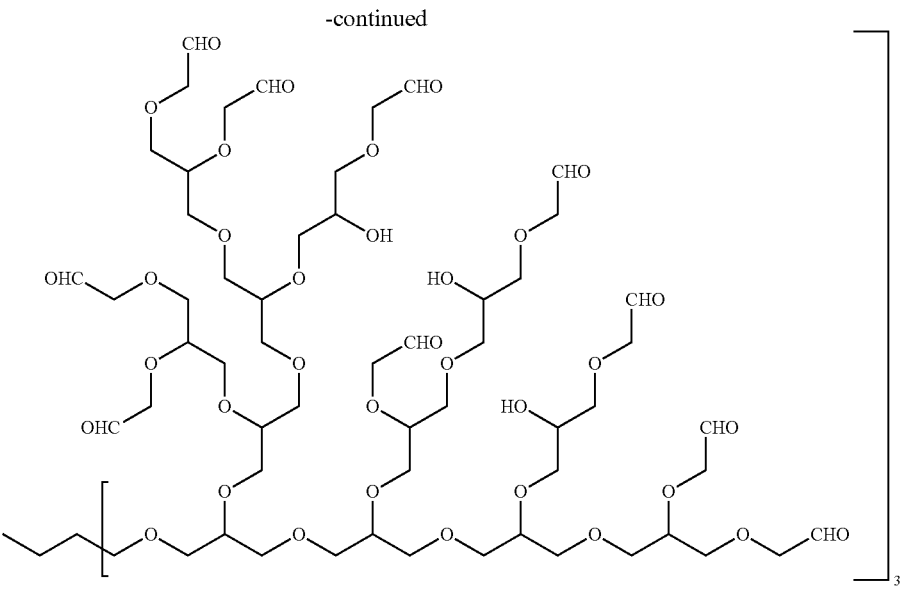

The degree of branching of the starting polyglycerol 5000 was calculated from its number average molecular weight ($M_n$) and its equivalent weight per terminal diol moiety, as described above.

A solution of 11.52 g of $NaIO_4$ in 50 mL of water was added to a solution of 10.06 g of polyglycerol 5000 (Hyperpolymers GmbH) dissolved in 30 mL of water, slowly enough to keep the reaction temperature from rising above 30° C. Once the addition was completed, the mixture was stirred at ambient temperature for 1 hour. Titration of an aliquot of the reaction mixture for iodate and residual iodate, according to the method of Belcher et al., supra, indicated that 74.9% of the periodate had been consumed and converted to iodate. The reaction solution was dialyzed (Visking Membra-Cel 3500/4, MWCO 3,500) for 2.5 days against 6, 7-L portions of deionized water, until treating a 1-mL aliquot of the dialyzate with 2 mL of 2.1 M chloroacetate buffer, pH 2.0, a pinch of potassium iodide and 6 drops of 1% starch gave no color. The solution in the dialysis tubing was frozen and lyophilized to give 4.89 g of polyglycerol aldehyde MW 5,000, EW 200, referred to herein as PGA-5-200.

Size exclusion chromatography with multi-angle light scattering detection (SEC-MALS) [mobile phase PBS (10 mM phosphate, 2.7 mM KCl, 0.137 M NaCl, pH 7.4), 0.5 mL/min, two TSKgel GMPWXL mixed-bed columns (TOSOH Bioscience LLC, Montgomeryville, Pa.), column temperature 30° C., dn/dc 0.124 mL/g] gave $M_n$ 5,000, $M_w$ 10,700 and $M_w/M_n$ 2.1. The polyglycerol aldehyde was characterized using $^1H$ NMR (500 MHz, $D_2O$).

Based on the quantity of periodate consumed (FW of $NaIO_4$ is 213.89) and the fact that each equivalent of periodate consumed results in the loss of an equivalent of methanol (FW 32.04) from the polymer, the equivalent weight (EW) per aldehyde was calculated as:

$$EW = \frac{\text{mass of polymer}}{\text{mole equivalents of aldehyde}}$$

$$= \frac{\text{mass of original polyglycerol} - \text{mass of equivalents of methanol lost}}{\text{mole equivalents of periodate consumed}}$$

$$= \frac{10.06 - 0.749 \times \frac{11.52}{213.89} \times 32.04}{0.749 \times \frac{11.52}{213.89}}$$

$$= 217$$

Example 5

Synthesis of Polyglycerol Aldehyde MW 5,000, EW 400

The purpose of this Example was to prepare a polyglycerol aldehyde having an average molecular weight of about 5,000 Da and an equivalent weight per aldehyde group of about 400 Da. The polyglycerol aldehyde was prepared by oxidizing polyglycerol having an average molecular weight of about 5,000 Da and a degree of branching of about 60% using sodium periodate. The degree of branching of the starting polyglycerol 5000 was calculated from its number average molecular weight ($M_n$) and its equivalent weight per terminal diol moiety, as described above.

A solution of 5.40 g of $NaIO_4$ in 31 mL of water was added to a solution of 10.92 g of polyglycerol 5000 (Hyperpolymers GmbH) dissolved in 30 mL of water, slowly enough to keep the reaction temperature from rising above 30° C. Once the addition was completed, the mixture was stirred at ambient temperature for half an hour and then dialyzed (Visking Membra-Cel 3500/4, MWCO 3,500) for 2.8 days against 7, 7-L portions of deionized water, until treating a 1-mL aliquot of the dialyzate with 2 mL of 2.1 M chloroacetate buffer, pH 2.0, a pinch of potassium iodide and 6 drops of 1% starch gave no color. The solution in the dialysis tubing was frozen and lyophilized to give 4.28 g of the polyglycerol aldehyde MW 5,000, EW 400, which was characterized using $^1H$ NMR (500 MHz, $D_2O$).

Using the method described in Example 4, the equivalent weight (EW) per aldehyde group was calculated as:

$$EW = \frac{10.92 - \frac{5.40}{213.89} \times 32.04}{\frac{5.40}{213.89}} = 400$$

SEC-MALS [mobile phase PBS (10 mM phosphate, 2.7 mM KCl, 0.137 M NaCl, pH 7.4), 0.5 mL/min, two TSKgel GMPWXL mixed-bed columns (TOSOH Bioscience LLC), column temperature 30° C., dn/dc 0.124 mL/g] gave $M_n$ 4,200, $M_w$ 11,200 and $M_w/M_n$ 2.6.

Example 6

Synthesis of Polyglycerol Aldehyde MW 5,000, EW 200

The purpose of this Example was to prepare a polyglycerol aldehyde having an average molecular weight of about 5,000 Da and an equivalent weight per aldehyde group of about 200 Da. The polyglycerol aldehyde was prepared by oxidizing polyglycerol having an average molecular weight of about 5,000 Da and a degree of branching of about 42% using sodium periodate and purified by a series of precipitations. The degree of branching of the starting polyglycerol 5000 was determined using the $^{13}$C NMR spectroscopy method described by A. Sunder et al. (*Macromolecules* 32:4240-4246, 1999). The polyglycerol 5000 was exhaustively oxidized, as in Example 4, to give a polyglycerol aldehyde having an equivalent weight per aldehyde of about 200 Da.

A solution of 50.00 g of NaIO$_4$ in 450 mL of water was added to a solution of 50.00 g of polyglycerol 5000 dissolved in 150 mL of water, slowly enough to keep the reaction temperature from rising above 30° C. Once the addition was completed, the mixture was stirred at ambient temperature for 1 hour. Ethylene glycol (3 mL) was added to quench excess periodate. The mixture was stirred at ambient temperature for half an hour, diluted with 2 L of isopropanol and filtered to remove precipitated salts. The mixture was concentrated by evaporating under reduced pressure to about 200 mL. Titration of an aliquot of the resulting mixture for residual iodate and periodate, according to the method of Belcher et al., supra, indicated the presence of 3.10 mmol of iodate and 0.135 mmol of periodate remaining in the product. Calcium chloride dihydrate (0.458 g, 3.12 mmol) and 500 mL of isopropanol were added to the mixture, which was then filtered through 20 g (2.5×0.875-inch pad) of Celite® 454 diatomaceous earth (World Minerals, Lompoc, Calif.). The mixture was concentrated by evaporating under reduced pressure, using additional water to ensure removal of isopropanol, and the resulting aqueous solution was lyophilized to give 46.4 g of the polyglycerol aldehyde MW 5,000, EW 200, which was charcterized using $^1$H NMR (500 MHz, D$_2$O).

SEC-MALS [mobile phase PBS (10 mM phosphate, 2.7 mM KCl, 0.137 M NaCl, pH 7.4), 0.5 mL/min, two TSKgel GMPWXL mixed-bed columns (TOSOH Bioscience LLC), column temperature 30° C., dn/dc 0.124 mL/g] gave $M_n$, 2,460, $M_w$ 8,580 and $M_w/M_n$ 3.5.

Example 7

Synthesis of Polyglycerol Aldehyde MW 10,000, EW 200

The purpose of this Example was to prepare a polyglycerol aldehyde having an average molecular weight of about 10,000 Da and an equivalent weight per aldehyde group of about 200 Da. The polyglycerol aldehyde was prepared by oxidizing polyglycerol having an average molecular weight of about 10,000 Da and a degree of branching of about 62% using sodium periodate. The degree of branching of the starting polyglycerol 10,000 was calculated from its number average molecular weight ($M_n$) and its equivalent weight per terminal diol moiety, as described above.

A solution of 45.37 g of NaIO$_4$ in 400 mL of water was added to a solution of 40.37 g of polyglycerol 10,000 dissolved in 120 mL of water, slowly enough to keep the reaction temperature from rising above 30° C. Once the addition was completed, the mixture was stirred at ambient temperature for 1 hour. Titration of an aliquot of the reaction mixture for iodate and residual periodate, according to the method of Belcher et al., supra, indicated that 82.8% of the periodate had been consumed and converted to iodate. Ethylene glycol (3 mL) was added to quench excess periodate. The mixture was stirred at ambient temperature for half an hour, diluted with 2 L of isopropanol and filtered to remove precipitated salts. The mixture was concentrated by evaporating under reduced pressure to about 230 mL. Titration of an aliquot of the resulting mixture for residual iodate and periodate, according to the method of Belcher et al., supra, indicated the presence of 1.89 mmol of iodate and 0.000 mmol of periodate remaining in the product. Calcium chloride dihydrate (0.279 g, 1.90 mmol) and 700 mL of isopropanol were added to the mixture, which was then filtered through 20 g (2.5×0.875-inch pad) of Celite® 454 diatomaceous earth. The mixture was concentrated by evaporating under reduced pressure, using additional water to ensure removal of isopropanol, and the resulting aqueous solution was lyophilized to give 35.8 g of the polyglycerol aldehyde MW 10,000, EW 200, which was characterized using $^1$H NMR (500 MHz, D$_2$O).

Using the method described in Example 4, the equivalent weight (EW) per aldehyde was calculated as:

$$EW = \frac{40.37 - 0.828 \times \frac{45.37}{213.89} \times 32.04}{0.828 \times \frac{45.37}{213.89}} = 198$$

SEC-MALS [mobile phase PBS (10 mM phosphate, 2.7 mM KCl, 0.137 M NaCl, pH 7.4), 0.5 mL/min, two TSKgel GMPWXL mixed-bed columns (TOSOH Bioscience LLC), column temperature 30° C., dn/dc 0.124 mL/g] gave $M_n$ 4,610, $M_w$ 8,510 and $M_w/M_n$ 2.1.

Example 8

Synthesis of Polyglycerol Aldehyde MW 10,000, EW 400

The purpose of this Example was to prepare a polyglycerol aldehyde having an average molecular weight of about 10,000 Da and an equivalent weight per aldehyde group of about 400 Da. The polyglycerol aldehyde was prepared by oxidizing polyglycerol having an average molecular weight of about 10,000 Da and a degree of branching of about 62% using sodium periodate. The degree of branching of the starting polyglycerol 10,000 was calculated from its number average molecular weight ($M_n$) and its equivalent weight per terminal diol moiety, as described above.

A solution of 21.39 g of NaIO$_4$ in 200 mL of water was added to a solution of 39.48 g of polyglycerol 10,000 dissolved in 120 mL of water, slowly enough to keep the reaction temperature from rising above 30° C. Once the addition was completed, the mixture was stirred at ambient temperature for 1 hour. Isopropanol (2 L) was added, and the mixture was filtered to remove precipitated salts. The mixture was concentrated by evaporating under reduced pressure to about 200 mL. Titration of an aliquot of the resulting mixture for residual iodate and periodate, according to the method of Belcher et al., supra, indicated the presence of 0.329 mmol of iodate and 0.000 mmol to of periodate remaining in the product. Calcium chloride dihydrate (0.050 g, 0.34 mmol) and 500 mL of isopropanol were added to the mixture, which was then filtered through 20 g (2.5×0.875-inch pad) of Celite® 454 diatomaceous earth. The mixture was concentrated by evaporating under reduced pressure, using additional water to ensure removal of isopropanol, and the resulting aqueous solution was lyophilized to give 17.4 g of the polyglycerol aldehyde MW 10,000, EW 400, which was characterized using $^1$H NMR (500 MHz, $D_2O$).

Using the method described in Example 4, the equivalent weight (EW) per aldehyde was calculated as:

$$EW = \frac{39.48 - \frac{21.39}{213.89} \times 32.04}{\frac{21.39}{213.89}} = 363$$

SEC-MALS [mobile phase PBS (10 mM phosphate, 2.7 mM KCl, 0.137 M NaCl, pH 7.4), 0.5 mL/min, two TSKgel GMPWXL mixed-bed columns (TOSOH Bioscience), column temperature 30° C., dn/dc 0.124 mL/g] gave $M_n$ 3,590, $M_w$ 5,440 and $M_w/M_n$ 1.5.

Examples 9 and 10

Stability of Polyglycerol Aldehyde MW 5,000 EW 200

The purpose of these Examples was to compare the stability of polyglycerol aldehyde, MW 5,000, EW 200, with dextran aldehyde D10-50 when stored in aqueous solution.

Aqueous solutions (25 wt % solids) of polyglycerol aldehyde, MW 5000, EW 200 (PGA-5-200) (Example 9), prepared according to Example 4, and dextran aldehyde D10-50 (Example 10, Comparative), prepared as described in Reagents, were incubated at 45° C. and periodically assayed for solution viscosity using a Brookfield viscometer. The molecular weight of the PGA-5-200 before and after aging at 45° C. was also determined by SEC-MALS. The viscosity results are summarized in Table 1. Whereas PGA-5-200 shows no loss of solution viscosity after 12 days, D10-50 shows second-order loss of solution viscosity with a half-life of 16 days. The $M_w$ of PGA-5-200, determined by SEC-MALS, before and after aging in solution at 45° C. for 12 days was 9,300 and 9,600, respectively, again indicating that PGA-5-200 is stable when stored in aqueous solution.

TABLE 1

Stability of Polyglycerol Aldehyde PGA-5-200 and Dextran Aldehyde D10-50 in Aqueous Solution, 45° C.

| Example | Test Substance | Age, Days | Viscosity, cP |
|---------|----------------|-----------|---------------|
| 9 | PGA-5-200 | 0 | 8.0 |
|   |           | 6 | 7.8 |
|   |           | 12 | 9.2 |

TABLE 1-continued

Stability of Polyglycerol Aldehyde PGA-5-200 and Dextran Aldehyde D10-50 in Aqueous Solution, 45° C.

| Example | Test Substance | Age, Days | Viscosity, cP |
|---------|----------------|-----------|---------------|
| 10, Comparative | D10-50 | 0 | 19.6 |
|                 |        | 6 | 13.9 |
|                 |        | 12 | 11.3 |

Examples 11 and 12

Stability of Polyglycerol Aldehyde MW 5,000 EW 200

The purpose of these Examples was to compare the molecular weight stability of polyglycerol aldehyde, MW 5,000, EW 200, with that of dextran aldehyde D10-50 when stored in aqueous solution. Weight-average molecular weights ($M_w$) were measured by SEC-MALS.

Aqueous solutions (25 wt % solids) of polyglycerol aldehyde, MW 5000, EW 200 (PGA-5-200) (Example 11), prepared according to Example 4, and dextran aldehyde D10-50 (Example 12, Comparative), prepared as described in Reagents, were incubated at 40° C. and periodically assayed for weight-average molecular weight ($M_w$) by SEC-MALS [mobile phase PBS (10 mM phosphate, 2.7 mM KCl, 0.137 M NaCl, pH 7.4), 0.5 mL/min, TSKgel G5000PWXL and G3000PWXL columns in series (TOSOH Bioscience, 1 each), column temperature 35° C., do/dc 0.124 mL/g]. The results are summarized in Table 2. Whereas PGA-5-200 shows no loss of $M_w$ after accelerated aging at 40° C., D10-50 shows an 11% decrease in $M_w$ after 7 days of accelerated aging at 40° C.

TABLE 2

Stability of Polyglycerol Aldehyde PGA-5-200 and Dextran Aldehyde D10-50 in Aqueous Solution at 40° C.

| Example | Test Substance | Age, Days | $M_w$ |
|---------|----------------|-----------|-------|
| 11 | PGA-5-200 | 0 | 10,700 |
|    |           | 4 | 10,455 |
|    |           | 6 | 10,670 |
|    |           | 7 | nd* |
|    |           | 8 | 10,970 |
| 12, Comparative | D10-50 | 0 | 9,900 |
|                 |        | 4 | nd |
|                 |        | 6 | nd |
|                 |        | 7 | 8,800 |
|                 |        | 8 | nd |

*nd means not determined.

Example 13

Hydrogel Formation

The purpose of this Example was to demonstrate the formation of a hydrogel by the reaction of a polyglycerol aldehyde and a multi-arm PEG amine.

An aqueous solution (100 μL) of a 25 wt % polyglycerol aldehyde MW 1,000, prepared as described in Example 2, was stirred together with 100 μL of a 50 wt % aqueous solution of eight-arm PEG 10K octaamine P8-10-1, prepared as described in Reagents. The results of six replicate gelation time measurements (i.e., mean and standard deviation) are given in Table 3

TABLE 3

Gelation Times for the Formation of a Hydrogel

| Time to string formation | 9.2 ± 0.8 sec |
|---|---|
| Time to fixed shape | 24.5 ± 1.4 sec |
| Time to tack-free | 38.2 ± 1.0 sec |

The results in Table 3 demonstrate that a hydrogel is formed within a short period of time by the reaction of polyglycerol aldehyde MW 1,000 and multi-arm PEG amine P8-10-1.

Examples 14-16

Hydrogel Formation Measured by Oscillating Disk Rheometry

The purpose of these Examples was to demonstrate the formation of a hydrogel by the reaction of a polyglycerol aldehyde and a multi-arm PEG amine. The formation of the hydrogel was measured by oscillating disk rheometry.

About 1.6 mL of an aqueous solution of polyglycerol aldehyde MW 5,000, EW 200 (PGA-5-200), prepared as described in Example 4, and about 1.6 mL of an aqueous solution containing eight-arm PEG octaamine P8-10-1, prepared as described in Reagents, were expressed from a 5-mL double-barreled syringe (Mixpac SDL X05-01-50M with plunger parts PLH X05-01-45M and PPD X05-01-02SM) through a 12-step static mixing tip (Mixpac ML 2.5-12-SM) onto the sample platform of a Model APA2000 rheometer (Alpha Technologies, Akron, Ohio). The two plates were brought together and values of storage modulus (G') were measured about every 2 seconds for a total of 3 minutes. The value of G' at 21 seconds was taken as a measure of speed of gelation. The results are shown in Table 4. Hydrogels having a range of acceptable mechanical properties can be generated by adjusting the concentrations and proportions of the polyglycerol aldehyde and the multi-arm PEG amine.

TABLE 4

Rheometry Results of Hydrogel Formation

| Example | PGA-5-200 (wt %) | P8-10-1 (wt %) | G' (21 sec) (kPa) |
|---|---|---|---|
| 14 | 25 | 50 | 66 |
| 15 | 25 | 30 | 44 |
| 16 | 20 | 20 | 14.3 |

Examples 17-24

In-Vitro Burst Testing of a Sealed Scalpel Incision

The purpose of these Examples was to demonstrate the burst strength of a seal of an incision in swine uterine horn using hydrogels formed from polyglycerol aldehydes and a multi-arm PEG amine.

Aqueous solutions of polyglycerol aldehydes, prepared according to Examples 3 through 5, were each loaded into one side of a double barreled syringe, as in Examples 14-16, and a 30 or 50 wt % aqueous solution of multi-arm PEG octaamine P8-10-1, prepared as described in Reagents, was loaded into the other side. A 12-step static mixing tip (Mixpac ML 2.5-12-LM) was attached to the nozzle of each syringe.

Fresh swine uterine horn, obtained from a local abattoir, was cut into 2 to 3-inch (5 to 7.5 cm) sections, and a 1-cm incision was made with scissors transverse to the lumen. A mixture of the two aqueous solutions described above was applied to the cut using a double-barreled syringe with mixing tip and allowed to cure for 1.0-1.5 min. The uterine horn section was then attached at one end to tubing connected to a syringe pump with pressure gauge. The uterine horn section was clamped shut at the other end, submerged in water, and purple-dyed water was pumped through the section at a rate of 10 mL/min. The pressure at which the seal burst and the mode of failure (cohesive versus adhesive) were noted. The results, given as mean and standard deviation, are summarized in Table 5.

TABLE 5

Results of Burst Pressure Measurements

| Example | Polyglycerol aldehyde (wt %) | P8-10-1 (wt %) | Burst Pressure (psi) | Failure |
|---|---|---|---|---|
| 17 | MW 2,000 EW 200 from Example 3 35% | 50 | 1.3 ± 0.2 (9.0 ± 1.4 kPa) | adhesive |
| 18 | MW 2,000 EW 200 from Example 3 25% | 50 | 2.3 ± 0.4 (15.9 ± 2.8 kPa) | cohesive |
| 19 | MW 2,000 EW 200 from Example 3 35% | 30 | 1.1 ± 0.6 (7.6 ± 4.1 kPa) | cohesive |
| 20 | MW 5,000 EW 400 from Example 5 30% | 50 | 2.7 ± 0.5 (18.6 ± 3.4 kPa) | cohesive |
| 21 | MW 5,000 EW 200 from Example 4 30% | 50 | 0.8 ± 0.4 (5.5 ± 2.8 kPa) | adhesive |
| 22 | MW 5,000 EW 200 from Example 4 25% | 50 | 4.0 ± 0.6 (27.6 ± 4.1 kPa) | adhesive |

For comparison, burst pressure measurements were made as described above using oxidized dextrans in place of the polyglycerol aldehydes. Specifically, an aqueous solution containing D10-20 or D10-50 (prepared as described in Reagents) was used in combination with an aqueous solution containing P8-10-1 PEG amine to seal an incision in swine uterine horn. The results are presented in Table 6.

TABLE 6

Comparative Results of Burst Pressure Measurements

| Example | dextran aldehyde (wt %) | P8-10-1 (wt %) | Burst Pressure (psi) | Failure |
|---|---|---|---|---|
| 23, Comparative | D10-20 EW 400 30% | 50 | 2.6 (18 kPa) | adhesive |
| 24, Comparative | D10-50 EW 150 30% | 50 | 2.9 (20 kPa) | adhesive |

The results shown in Table 5 demonstrate that hydrogel adhesives formed from polyglycerol aldehydes and multi-arm PEG amines exhibit burst strengths that are adequate for tissue adhesive, sealant and other in vivo applications. Comparison of the results shown in Table 5 with the results shown in Table 6 demonstrate that polyglycerol aldehydes, when combined with a water-dispersible multi-arm polyether amine, produce tissue adhesives with adhesive strengths similar to or greater than those of comparable formulations produced with an oxidized polysaccharide (Comparative Examples 23 and 24).

Example 25

Cytotoxicity Testing of Hydrogels

The purpose of this Example was to demonstrate the safety of hydrogels formed from a polyglycerol aldehyde and a multi-arm PEG amine in an in vitro cytotoxicity test.

Double-barreled 5-mL syringes and plunger parts, as in Examples 14-16, and 12-step static mixing tips (Mixpac ML 2.5-12-LM) were sealed in protective pouches and sterilized by autoclaving. An aqueous solution of 25 wt % polyglycerol aldehyde MW 5,000, EW 200 (PGA-5-200), prepared according to Example 4, and aqueous solutions of 20 and 30 wt % 8-arm PEG 10K octaamine P8-10-1, prepared as described in Reagents, were sterile filtered (0.2 µm) and then manipulated within a sterile hood. The polyglycerol aldehyde solution was loaded into one side of a double barreled syringe, and the 20 or 30 wt % P8-10-1 solution was loaded into the other side. A 12-step static mixing tip was attached to the nozzle of each syringe.

Flat strips of adhesive hydrogel were extruded from each double-barreled syringe through the static mixing tip into the well of a sterile polystyrene culture plate. Using sterile technique, a 30 mg sample of each hydrogel was transferred into a 35 mm-diameter well of a sterile polystyrene culture plate and covered with 2 mL of Dulbecco's modified essential medium (DMEM) supplemented with 10% fetal calf serum. The well was then seeded with 1 mL (50,000 to 100,000 cells) of an overnight culture of NIH3T3 mouse fibroblast cells, obtained from the American Type Culture Collection (ATCC; Manassas, Va.) and grown in DMEM supplemented with 10% fetal calf serum. After 24 and 48 hours of incubation at 37° C., the cells were examined for cell rounding (indicating death), confluent coating of the well bottom, growth up to the edges of the hydrogel, and overgrowth of the hydrogel (indicating adhesion of cell cultures to the hydrogel). Tests were run in triplicate. Cells incubated in the absence of hydrogel served as a positive control for cell viability, and cells incubated in the presence of a 1 cm×1 cm strip of PVC (polyvinyl chloride) according to ISO 10993-5:1999 served as a negative control for cell viability. Hydrogels formed from both 25 wt % polyglycerol aldehyde plus 20 wt % PEG amine solutions, and 25 wt % polyglycerol aldehyde plus 30 wt % PEG amine solutions showed no sign of cytotoxicity toward NIH3T3 mouse fibroblasts according to this assay. Cells formed confluent monolayers, comparable to the positive control that extended to, but did not overgrow the hydrogel samples. These results suggest that hydrogels formed from polyglycerol aldehydes and multi-arm PEG amines are safe for use in the body.

Examples 26-27

In Vitro Degradation of Hydrogels

The purpose of these Examples was to demonstrate the degradation over time of hydrogels formed from a polyglycerol aldehyde and a multi-arm PEG amine in an in vitro degradation test.

One barrel of a double-barreled 5-mL syringe, as in Examples 14-16, was loaded with a 20 or 25 wt % solution of polyglycerol aldehyde MW 5,000, EW 200, prepared according to Example 4. The other barrel was loaded with a 25 wt % solution of a 5:1 (w/w) mixture of 8-arm PEG 10K octaamine P8-10-1, prepared as described in Reagents, and 8-arm PEG 10K hexadecamine P8-10-2, prepared as described in Reagents. A 12-step static mixing tip (MixPac ML 2.5-12-SM) was attached to each syringe. Hydrogel was extruded from each double-barreled syringe through the mixing tip into a Teflon® mold to create strips approximately 30 mm×7 mm×1 mm. Each strip was cured for 15 min before being removed from the mold. Each test strip was individually placed in a pre-wetted, tared stainless steel mesh (#400) cup, and the cup plus sample was weighed, placed in a 20-mL scintillation vial and covered with about 18 mL of Dulbecco's phosphate buffered saline (DPBS). The capped vials, each containing a test strip plus mesh cup, were incubated at 37° C. and 105 rpm in an orbital shaker. Periodically, each mesh cup with test strip was removed from its vial, patted dry with a paper towel, weighed, returned to its vial and covered with about 18 mL of fresh DPBS. Each vial was then capped and returned to the orbital shaker. Duplicate test strips of each formulation were run. The masses of duplicate test strip recorded at each time point were averaged, and the results are summarized in Table 7.

These Examples demonstrate that hydrogels formed from a polyglycerol aldehyde and multi-arm PEG amines persist in an aqueous environment for days but degrade over time.

TABLE 7

| Mass of Hydrogel Samples (% of original) During In vitro Degradation[a] | | | | | | |
|---|---|---|---|---|---|---|
| | wt % polyglycerol aldehyde MW | | | time, hours | | |
| Example | 5,000, EW 200[b] | 0 | 5 | 24 | 48 | 168 | 192 |
| 26 | 20 | 100 | 144 | 130 | 116 | 82 | 70 |
| 27 | 25 | 100 | 237 | 221 | 195 | 152 | 138 |

[a]Masses (% of original) are the mean of duplicate runs.
[b]Wt % of polyglycerol aldehyde MW 5,000, EW 200, in solution before being combined with PEG amine. Each hydrogel was formed by mixing the solution of polyglycerol aldehyde MW 5,000, EW 200, with a 25 wt % solution of 5:1 (w/w) P8-10-1:P8-10-2.

What is claimed is:
1. A kit comprising:
   a) at least one polyglycerol aldehyde having aldehyde groups, said polyglycerol aldehyde having a number-average molecular weight of about 400 to about 20,000 Daltons the general formula:

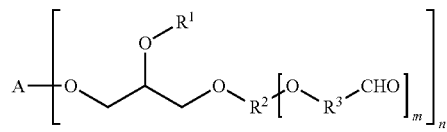

wherein;

A is either (a) a hydrocarbyl group derived by removing on or more hydroxyl groups from an alcohol or polyol containing 1 to 20 carbon atoms and 1 to 8 hydroxyl groups or (b) an oxahydrocarbyl or polyoxahydrocarbyl group derived by removing or more hydroxyl groups from the reaction product of (I) an alcohol or polyol containing 1 to 20 carbon atoms and 1 to 8 hydroxyl groups and (II) one or more cyclic ethers, wherein the $M_n$ of the reaction product is less than or equal to 5,000 Da;

$R^1$ is a hydrogen atom, a 1 to 8-carbon hydrocarbyl group, $R^2$—O—[$R^3$—CHO]$_p$, or $R^3$—CHO;

$R^2$ is a polymeric segment comprising 1 to 270 glycerol units connected by ether linkages;

$R^3$ is a hydrocarbylene group containing 1 to 8 carbon atoms;

n=1 to 8; m*n=3 to 170; and p=1 to 40, wherein n, m and p are intergers; and an equivalent weight per aldehyde group of about 100 to about 3,000 Daltons; and b) at least one water-dispersible, multi-arm amine wherein at least three of the arms are terminated by at least one primary amine group, wherein the multi-arm amine has a number-average molecular weight of about 450 to about 200,000 Daltons.

2. The kit according to claim 1 wherein the polyglycerol aldehyde is contained in a first aqueous solution or dispersion and the water-dispersible, multi-arm amine is contained in a second aqueous solution or dispersion.

3. The kit according to claim 2 wherein the first aqueous solution or dispersion contains the polyglycerol aldehyde at a concentration of about 5% to about 40% by weight relative to the total weight of the solution or dispersion.

4. The kit according to claim 2 wherein the second aqueous solution or dispersion contains the water-dispersible, multi-arm amine at a concentration of about 5% to about 70% by weight relative to the total weight of the solution or dispersion.

5. The kit according to claim 1 wherein the cyclic ethers are selected from the group consisting of oxirane, methyloxirane, oxetane and oxolane.

6. The kit according to claim 1 wherein in the general formula A is $CH_3CH_2C(CH_2—)_3$, derived by removing three hydroxyl groups from trimethylolpropane; $R^2$ is a polymeric segment consisting of 1 to 60 glycerol units connected by ether linkages; $R^3$ is $—CH_2—$; $R^1$ is a hydrogen atom, $R^2—O—[R^3—CHO]_p$, or $R^3—CHO$; m=1 to 30; n=3; and p=1 to 30.

7. The kit according to claim 1 wherein the polyglycerol aldehyde has a degree of branching of about 10% to about 99.9%.

8. The kit according to claim 1 wherein the water-dispersible, multi-arm amine is selected from the group consisting of water dispersible multi-arm polyether amines, amino-terminated dendritic polyamidoamines, and multi-arm branched end amines.

9. The kit according to claim 1 wherein the water-dispersible, multi-arm amine is a water dispersible multi-arm polyether amine.

10. The kit according to claim 9 wherein the water dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

11. A dried hydrogel formed by a process comprising the steps of:

a) combining in a solvent (i) at least one polyglycerol aldehyde having aldehyde groups, said polyglycerol aldehyde having a number-average molecular weight of about 400 to about 20,000 Daltons the general formula:

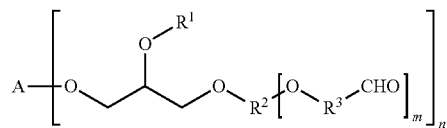

wherein:
A is either (a) a hydrocarbyl group derived by removing on or more hydroxyl groups from an alcohol or polyol containing 1 to 20 carbon atoms and 1 to 8 hydroxyl groups or (b) an oxahydrocarbyl or polyoxahydrocarbyl group derived by removing or or more hydroxyl groups from the reaction product of (I) an alcohol or polyol containing 1 to 20 carbon atoms and 1 to 8 hydroxyl groups and (II) one or more cyclic ethers, wherein the $M_n$ of the reaction product is less than or equal to 5,000 Da;
$R^1$ is a hydrogen atom, a 1 to 8-carbon hydrocarbyl group, $R^2—O—[R^3—CHO]_p$, or $R^3—CHO$;
$R^2$ is a polymeric segment comprising 1 to 270 glycerol units connected by ether linkages;
$R^3$ is a hydrocarbylene group containing 1 to 8 carbon atoms;
n=1 to 8; m*n=3 to 170; and p=1 to 40, wherein n, m and p are intergers; and an equivalent weight per aldehyde group of about 100 to about 3,000 Daltons; with (ii) at least one water-dispersible, multi-arm amine, wherein at least three of the arms are terminated by at least one primary amine group, said multi-arm amine having a number-average molecular weight of about 450 to about 200,000 Daltons, to form a hydrogel; and b) treating said hydrogel to remove at least a portion of said solvent to form the dried hydrogel.

12. The dried hydrogel according to claim 11 wherein said dried hydrogel is in the form of a film.

13. The dried hydrogel according to claim 11 wherein the process further comprises the step of comminuting the dried hydrogel to form finely divided particles.

14. A composition comprising the reaction product of:

a) at least one polyglycerol aldehyde having aldehyde groups, said polyglycerol aldehyde having a number-average molecular weight of about 400 to about 20,000 Daltons the general formula:

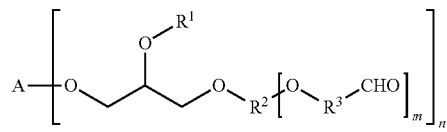

wherein;
A is either (a) a hydrocarbyl group derived by removing on or more hydroxyl groups from an alcohol or polyol containing 1 to 20 carbon atoms and 1 to 8 hydroxyl groups or (b) an oxahydrocarbyl or polyoxahydrocarbyl group derived by removing or or more hydroxyl groups from the reaction product of (I) an alcohol or polyol containing 1 to 20 carbon atoms and 1 to 8 hydroxyl groups and (II) one or more cyclic ethers, wherein the $M_n$ of the reaction product is less than or equal to 5,000 Da;

R¹ is a hydrogen atom, a 1 to 8-carbon hydrocarbyl group, R²—O—[R³—CHO]$_p$, or R³—CHO;

R² is a polymeric segment comprising 1 to 270 glycerol units connected by ether linkages;

R³ is a hydrocarbylene group containing 1 to 8 carbon atoms;

n=1 to 8; m*n=3 to 170; and p=1 to 40, wherein n, m and p are intergers; and an equivalent weight per aldehyde group of about 100 to about 3,000 Daltons; and b) at least one water-dispersible, multi-arm amine wherein at least three of the arms are terminated by at least one primary amine group, said multi-arm amine having a number-average molecular weight of about 450 to about 200,000 Daltons.

15. A crosslinked hydrogel composition comprising:

a) at least one polyglycerol aldehyde having aldehyde groups, said polyglycerol aldehyde having a number-average molecular weight of about 400 to about 20,000 Daltons the general formula:

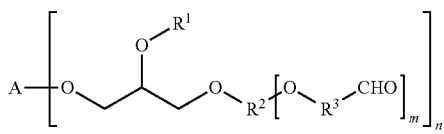

wherein:

A is either (a) a hydrocarbyl group derived by removing on or more hydroxyl groups from an alcohol or polyol containing 1 to 20 carbon atoms and 1 to 8 hydroxyl groups or (b) an oxahydrocarbyl or polyoxahydrocarbyl group derived by removing or or more hydroxyl groups from the reaction product of (I) an alcohol or polyol containing 1 to 20 carbon atoms and 1 to 8 hydroxyl groups and (II) one or more cyclic ethers, wherein the $M_n$ of the reaction product is less than or equal to 5,000 Da;

R¹ is a hydrogen atom, a 1 to 8-carbon hydrocarbyl group, R²—O—[R³—CHO]$_p$, or R³—CHO;

R² is a polymeric segment comprising 1 to 270 glycerol units connected by ether linkages;

R³ is a hydrocarbylene group containing 1 to 8 carbon atoms;

n=1 to 8; m*n=3 to 170; and p=1 to 40, wherein n, m and p are intergers; and an equivalent weight per aldehyde group of about 100 to about 3,000 Daltons; and b) at least one water-dispersible, multi-arm amine wherein at least three of the arms are terminated by at least one primary amine group, said multi-arm amine having a number-average molecular weight of about 450 to about 200,000 Daltons;

wherein said at least one polyglycerol aldehyde and said at least one water-dispersible, multi-arm amine are crosslinked through covalent bonds formed between the aldehyde groups of the polyglycerol aldehyde and the primary amine groups of the water-dispersible, multi-arm amine.

16. The crosslinked hydrogel composition according to claim 15 wherein the cyclic ethers are selected from the group consisting of oxirane, methyloxirane, oxetane and oxolane.

17. The crosslinked hydrogel composition according to claim 15 wherein in the general formula A is CH₃CH₂C(CH₂—)₃, derived by removing three hydroxyl groups from trimethylolpropane; R² is a polymeric segment consisting of 1 to 60 glycerol units connected by ether linkages; R³ is —CH₂—; R¹ is a hydrogen atom, R²—O—[R³—CHO]$_p$, or R³—CHO; m=1 to 30; n=3; and p=1 to 30.

18. The crosslinked hydrogel composition according to claim 15 wherein the water-dispersible, multi-arm amine is selected from the group consisting of water dispersible multi-arm polyether amines, amino-terminated dendritic polyamidoamines, and multi-arm branched end amines.

19. The crosslinked hydrogel composition according to claim 15 wherein the water-dispersible, multi-arm amine is a water dispersible multi-arm polyether amine.

20. The crosslinked hydrogel composition according to claim 19 wherein the water dispersible multi-arm polyether amine is selected from the group consisting of amino-terminated star polyethylene oxides, amino-terminated dendritic polyethylene oxides, amino-terminated comb polyethylene oxides, amino-terminated star polypropylene oxides, amino-terminated dendritic polypropylene oxides, amino-terminated comb polypropylene oxides, amino-terminated star polyethylene oxide-polypropylene oxide copolymers, amino-terminated dendritic polyethylene oxide-polypropylene oxide copolymers, amino-terminated comb polyethylene oxide-polypropylene oxide copolymers, and polyoxyalkylene triamines.

21. A method for applying a coating to an anatomical site on tissue of a living organism comprising:

applying to the site a) at least one polyglycerol aldehyde having aldehyde groups, said polyglycerol aldehyde having a number-average molecular weight of about 400 to about 20,000 Daltons the general formula:

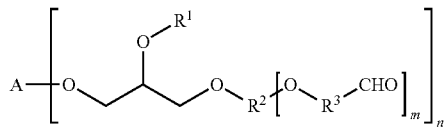

wherein:

A is either (a) a hydrocarbyl group derived by removing on or more hydroxyl groups from an alcohol or polyol containing 1 to 20 carbon atoms and 1 to 8 hydroxyl groups or (b) an oxahydrocarbyl or polyoxahydrocarbyl group derived by removing or or more hydroxyl groups from the reaction product of (I) an alcohol or polyol containing 1 to 20 carbon atoms and 1 to 8 hydroxyl groups and (II) one or more cyclic ethers, wherein the $M_n$ of the reaction product is less than or equal to 5,000 Da;

R¹ is a hydrogen atom, a 1 to 8-carbon hydrocarbyl group, R²—O—[R³—CHO]$_p$, or R³—CHO;

R² is a polymeric segment comprising 1 to 270 glycerol units connected by ether linkages;

R³ is a hydrocarbylene group containing 1 to 8 carbon atoms;

n=1 to 8; m*n=3 to 170; and p=1 to 40, wherein n, m and p are intergers; and an equivalent weight per aldehyde group of about 100 to about 3,000 Daltons;

followed by b) at least one water-dispersible, multi-arm amine wherein at least three of the arms are terminated by a primary amine group, said multi-arm amine having a number-average molecular weight of about 450 to about 200,000 Daltons, or (b) followed by (a), or premixing (a) and (b);

and applying the resulting mixture to the site before the resulting mixture completely cures.

22. The method according to claim 21 wherein the cyclic ethers are selected from the group consisting of oxirane, methyloxirane, oxetane and oxolane.

23. The method according to claim 21 wherein in the general formula A is $CH_3CH_2C(CH_2-)_3$, derived by removing three hydroxyl groups from trimethylolpropane; $R^2$ is a polymeric segment consisting of 1 to 60 glycerol units connected by ether linkages; $R^3$ is $-CH_2-$; $R^1$ is a hydrogen atom, $R^2-O-[R^3-CHO]_p$, or $R^3-CHO$; m=1 to 30; n=3; and p=1 to 30.

* * * * *